(12) United States Patent
Otani et al.

(10) Patent No.: US 6,562,981 B2
(45) Date of Patent: May 13, 2003

(54) BENZO (4,5) IMIDAZO (2,1-A) ISOINDOL-11-ONES

(75) Inventors: Junji Otani, Kobe (JP); Kazuhiko Kunimoto, Takatsuki (JP); Takashi Deno, Nishinomiya (JP); Brian Gerrard Devlin, Takarazuka (JP); Kunihiko Kodama, Takarazuka (JP)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/135,809

(22) Filed: Apr. 30, 2002

(65) Prior Publication Data

US 2003/0023097 A1 Jan. 30, 2003

Related U.S. Application Data

(62) Division of application No. 09/017,872, filed on Feb. 3, 1998, now Pat. No. 6,413,655.

(30) Foreign Application Priority Data

| Feb. 3, 1997 | (EP) | 97810049 |
|---|---|---|
| Feb. 3, 1997 | (EP) | 97810050 |
| Feb. 3, 1997 | (EP) | 97810051 |
| Feb. 4, 1997 | (EP) | 97810054 |
| Feb. 4, 1997 | (EP) | 97810055 |

(51) Int. Cl.[7] ........................... C07D 235/02
(52) U.S. Cl. ................................... 548/301.7
(58) Field of Search .................. 548/301.7

(56) References Cited

U.S. PATENT DOCUMENTS

| 5,227,252 A | 7/1993 | Murayama et al. | 428/690 |
|---|---|---|---|
| 5,256,192 A | 10/1993 | Liu et al. | 106/21 A |
| 5,281,489 A | 1/1994 | Mori et al. | 428/690 |
| 5,294,810 A | 3/1994 | Egusa et al. | 257/40 |
| 5,431,845 A | 7/1995 | Akhavan-Tafti | 252/700 |
| 5,593,788 A | 1/1997 | Shi et al. | 428/690 |
| 5,856,508 A | * 1/1999 | Jaffe et al. | 548/301.7 |
| 6,080,516 A | 6/2000 | Devlin et al. | 430/17 |
| 6,103,446 A | 8/2000 | Devlin et al. | 430/270.1 |
| 6,146,809 A | 11/2000 | Devlin et al. | 430/270.1 |

FOREIGN PATENT DOCUMENTS

| EP | 0456609 | 11/1991 |
|---|---|---|
| EP | 0766498 | 4/1997 |
| GB | 2292947 | 3/1996 |
| JP | 59/185349 | * 10/1984 |
| JP | 6228546 | 8/1994 |
| JP | 06/228546 | * 8/1994 |
| WO | 93/23492 | 11/1993 |
| WO | 94/15441 | 7/1994 |

OTHER PUBLICATIONS

Derwent Abstr. 94–018671 [03] for JP 05320633 (1993).
Harris et al., ACS Symp. Ser. 132, (1980) pp. 39–45.
Port et al., "Host–Guest Energy Transfer via Dipole–Dipole Interaction in Doped Fluorene Crystals", Z. Naturforsch, 36a (1981), pp. 697–704.
Tang et al., "Electroluminescense of Doped Organic Thin Films", J. Appl. Phys. 65 (9), May 1989, pp. 3610–3616.
Lang et al., "High–Pressure Study of Energy Transfer between Coumarin 138 and Rhodamine B in a solid Polymer Matrix", J. Phys. Chem., vol. 97, No. 19, (1993), pp. 5058–5064.

* cited by examiner

*Primary Examiner*—Laura L. Stockton
(74) *Attorney, Agent, or Firm*—David R. Crichton

(57) ABSTRACT

A composition comprising (a) an effective amount of a guest chromophore embedded in a matrix of a host chromophore, or (b) a host chromophore and an effective amount of a guest chromophore both embedded in a polymer matrix, wherein the absorption spectrum of the guest chromophore overlaps with the fluorescence emission spectrum of the host chromophore, and wherein the host chromophore is selected from the group consisting of benzo [4,5]imidazo[2,1-a] isoindol-11-ones.

2 Claims, No Drawings

BENZO (4,5) IMIDAZO (2,1-A) ISOINDOL-11-ONES

This is a divisional of application Ser. No. 09/017,872, filed on Feb. 3, 1998 now U.S. Pat. No. 6,413,655.

The present invention relates to a composition comprising (a) an effective amount of a guest chromophore embedded in a matrix of a host chromophore, or (b) a host chromophore and an effective amount of a guest chromophore both embedded in a polymer matrix, wherein the absorption spectrum of the guest chromophore overlaps with the fluorescence emission spectrum of the host chromophore, and wherein the host chromophore is selected from the group consisting of benzo [4,5]imidazo [2,1-a] isoindol-11-ones.

Further, the present invention relates to a process for the preparation of this composition, a polymerisable composition comprising this composition, a composition comprising a carrier material with a high relief of a polymerized photoresist material containing this composition, a process for the preparation of fluorescent high relief images on a carrier, the use of the compositions as fluorescent materials, especially in electroluminescent devices, and novel non-functionalized benzo[4,5]imidazo[2,1-a] isoindol-11-one derivatives.

Combinations comprising host chromophores with guest chromophores dissolved therein to generate materials with enhanced fluorescence and large differences between absorption maximum and emission maximum are highly desired materials that possess a wide range of potential and actual technical applications. The large difference between the absorption (excitation) maximum and the emission maximum is due to the occurrence of resonant energy transfer between the respective host and guest chromophores.

The possibility of energy transfer between chromophores that possess an area of overlap of the absorption spectrum of a guest chromophore with the fluorescence emission spectrum of a host is known. For example, H. Port et al. describe in Z. Naturforsch., 36a, pages 697 to 704 (1981) mixed crystals of fluorene doped with dibenzofurane or benzindan with an enhanced fluorescence in the UV region at temperatures below 100 K. However, the low temperature fluorescence has no practical value and is only of scientific interest.

C. W. Tang et al. disclose in J. Appl. Phys., 65, 3610 to 3616 (1989) a multilayered electroluminescent device with a light emitting layer composed of 8-hydroxyquinoline aluminum, in which is embedded a zone doped with a fluorescent molecule such as coumarin. The device shows improved electroluminescence and an effective Stoke's color shift which is dependent on the particular dopant. The manufacture of the device is complicated and not readily suitable for an industrial production.

J. M. Lang et al. describe in J. Phys. Chem. 97, pages 5058 to 5064 (1993) the combination of coumarin as host and rhodamine as guest whereby both components are dissolved in polyacrylic acid, but Lang's study demonstrates enhanced fluorescence only under high pressure.

In WO 93/23492 are disclosed fluorescent microparticles with an enhanced Stokes shift, which are composed of soluble and fluorescent host and guest dyes absorbed or bonded to polymeric microparticles. The material is used for the optical detection of nucleic acids like DNA or RNA. Unfavorably, the solid state fluorescence of these microparticles is poor.

U.S. Pat. No. 5,227,252 discloses a fluorescent composition of 8-hydroxyquinoline aluminum as host and quinacridones as guest. Similarly, JP-A-05 320 633 discloses a fluorescent composition of 8-hydroxyquinoline aluminum as host and diketopyrrolopyrroles as guest. However, in both documents, the guests are insoluble materials, they are dissolved mainly as microsized clusters. The occurrence of microsized clusters is due to co-sublimation processes being the means of preparation. The materials possess a larger Stoke's shifts than would be anticipated by normal single component fluorescent materials, and are used for example as light emitting materials in electroluminescent devices. The process for their manufacture requires large expenditures on technical equipment to ensure the careful control process conditions such as vacuum and temperature, to achieve the desired mixed material. The process is not convenient for large scale industrial manufacture.

In EP-A-0 456 609 is disclosed a process for the preparation of 1,2,3,4-tetrachloro-benzo[4,5]imidazo[2,1-a] isoindol-11-one and its derivatives in the presence of selected solvents. These compounds are pigments showing solid state fluorescence and improved outdoor durability. It is also mentioned therein, that the combination of 95% of the yellow 1,2,3,4-tetrachlorobenzo[4,5]imidazo[2,1-a] isoindol-11-one with 5% of Indanthrone Blue generates a green fluorescent pigment. Hence, such a system is a pigment composite, wherein the new color generated is simply a sum of the two component colors. The color is not created by virtue of the occurrence of complex, molecular level, energy transfer processes that require close interaction between the components of the mixture.

F. W. Harris et. al. describe in ACS Symp. Ser. 132, 39 (1980) the compound 1,2,3,4-tetraphenyl-benzo [4,5] imidazo [2,1-a] isoindol-11-one as a model material, as a part of their investigations into phenylated polyimidazopyrrolones for potential use in aerospace applications. However, no reference to its fluorescence behavior is made.

Hence, the object of the invention on hand was to find a fluorescent composition, which does not show the above mentioned disadvantages, preferably a composition should be provided which has a greatly enhanced and intense fluorescence emission,
shows an intense solid state fluorescence, wherein the emission spectrum is preferably in the visible region of the electromagnetic spectrum,
is excitable using wavelengths in both the UV and visible regions,
shows a very excellent photostability and outdoor durability,
shows a wide range of emission spectra through selection of suited guest molecules (color tuning),
has a high thermal stability,
is easily prepared, i.e. by a (co-) precipitation process,
can be used for the preparation of electroluminescence devices, if the host chromophore is selected from the group consisting of benzo[4,5]imidazo[2,1-a]isoindol-11-ones, which means derivatives of benzo[4,5]imidazo[2,1-a]isoindol-11-one as the fundamental substance.

In addition, the enhancement factor for the present compositions preferably should be all positive and should be at least 1.3, more preferably at least 2 and most preferably at least 5. The term "enhancement factor" as used herein, is defined as the increased or decreased factor, in terms of peak height emission intensities of a solid-state powder comprising of host and guest fluorescent moieties compared to an identical powder that does not contain any fluorescent guest moieties. Comparisons are considered real, for as long as the excitation radiation wavelengths are identical. In general, the emission wavelengths of host/guest material occur at longer wavelengths (lower energy) as compared to an identical material with no guest component.

Accordingly, a composition was found comprising (a) an effective amount of a guest chromophore embedded in a matrix of a host chromophore, or (b) a host chromophore and an effective amount of a guest chromophore both embedded in a polymer matrix, wherein the absorption spectrum of the guest chromophore overlaps with the fluorescence emission spectrum of the host chromophore, and wherein the host chromophore is selected from the group consisting of benzo[4,5] imidazo [2,1-a] isoindol-11-ones.

In addition, a process for the preparation of this composition, a polymerizable composition comprising this composition, a composition comprising a carrier material with a high relief of a polymerized photoresist material containing this composition, a process for the preparation of fluorescent high relief images on a carrier, the use of the compositions as fluorescent materials, esp. in electroluminescent devices, and novel non-functionalized benzo[4,5] imidazo[2,1-a]isoindol-11-one derivatives were found, too.

A first embodiment of the present invention relates to a composition comprising (a) an effective amount of a guest chromophore embedded in a matrix of a host chromophore, or (b) a host chromophore and an effective amount of a guest chromophore both embedded in a polymer matrix, wherein the absorption spectrum of the guest chromophore overlaps with the fluorescence emission spectrum of the host chromophore, and wherein the host chromophore is selected from the group consisting of benzo [4,5] imidazo [2,1-a] isoindol-11-ones.

The host chromophore is selected from the group consisting of derivatives of benzo[4,5]imidazo[2,1-a]isoindol-11-one and benzo[4,5]imidazo[2,1-a]isoindol-11-one (hereinafter referred to as benzoimidazoisoindolone(s)) itself. The compounds are preferably derivatives that are soluble in an organic or aqueous solvent.

Under the aspects of the invention solubility of host chromophores means preferably that at least 10 mg, more preferably at least 50 mg and most preferably at least 100 mg of the benzoimidazoisoindolone derivative are soluble in 1 liter of solvent like dimethylformamide, at 20° C. It is self-evident, that the solubilities are higher at increasing temperatures and depend on the choice of a solvent.

The benzoimidazoisoindolones may correspond to the formula I

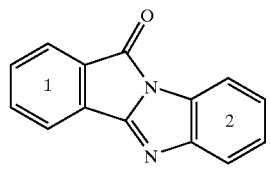

wherein
the neighboring carbon atoms of the benzene rings 1 and 2
  are uncondensed or condensed with benzene rings, heteroaromatic rings, aliphatic rings, or heteroaliphatic rings, and wherein the benzene rings 1 or 2 or both, the condensed ring moieties or all are unsubstituted or substituted with organic groups and/or halogen atoms.

The groups forming a condensed ring are preferably selected from the group consisting of bivalent residues of formulae —CH=CH—CH=CH—, —CH=CH—N=CH—, —CH=CH—CH=N—, —CH=N—CH=N—, —CH=CH—NR$_1$—, —CH=N—CH$_2$—, —CH=CH—S—, —CH=CH—O—, —(CH$_2$)$_3$—, —(CH$_2$)$_4$—, —CH$_2$—CH$_2$—NR$_1$—CH$_2$—, —CH$_2$—CH$_2$—CH$_2$—NR$_1$—, —CH$_2$—CH$_2$—O—CH$_2$ —, —CH$_2$—CH$_2$—CH$_2$—O—, —CH$_2$—CH$_2$—S—CH$_2$—, —CH$_2$—CH$_2$—CH$_2$S—, —CH$_2$—O—CH$_2$—, —CH$_2$—CH$_2$—O—, —CH$_2$—S—CH$_2$—, and —CH$_2$—CH$_2$—S—, wherein R$_1$ is H or an organic substituent, and the bivalent residues are unsubstituted or substituted with an organic group.

R$_1$, as organic substituent, may be linear or branched C$_1$ to C$_{20}$alkyl, C$_5$ to C$_7$cycloalkyl, benzyl or R$_2$—C(O)—, wherein R$_2$ is C$_1$ to C$_{20}$alkyl, which is unsubstituted or substituted with F, Cl or C$_1$ to C$_{12}$alkoxy, or C$_5$ to C$_7$cycloalkyl, phenyl or benzyl, which are is unsubstituted or substituted with F, Cl, C$_1$ to C$_{12}$alkyl, or C$_1$ to C$_{12}$alkoxy.

Preferred examples for R$_1$ are H, methyl, ethyl, propyl, butyl, pentyl, hexyl, benzyl, methylbenzyl, dimethylbenzyl, acetyl, propionyl, butyroyl, benzyl-C(O)—, phenyl-C(O)—, toluyl-C(O)—, mono-, di- or tri-chloroacetyl, and mono-, di- or tri-fluoroacetyl, mono- and dichlorophenyl-C(O)—.

The organic substituent may be selected from the group consisting of halogen, —CN, —NO$_2$, C$_1$ to C$_{18}$ alkyl, C$_2$ to C$_{18}$alkenyl, C$_2$ to C$_{18}$alkinyl, C$_1$ to C$_{18}$ hydroxyalkyl, C$_1$ to C$_{18}$ halogenalkyl, C$_3$ to C$_{12}$ cycloalkyl, C$_6$ to C$_{18}$ aryl, C$_5$ to C$_{17}$ heteroaryl, C$_3$ to C$_{12}$ cycloalkylalkyl, C$_6$ to C$_{18}$ aralkyl, C$_5$ to C$_{17}$ heteroaralkyl, C$_1$ to C$_{18}$ alkyloxy, C$_3$ to C$_{12}$ cycloalkyloxy C$_6$ to C$_{18}$ aryloxy, C$_5$ to C$_{17}$ heteroaryloxy, C$_3$ to C$_{12}$ cycloalkylalkyloxy, C$_6$ to C$_{18}$ aralkyloxy, C$_5$ to C$_{17}$ heteroaralkyloxy, C$_1$ to C$_{18}$ alkylthio, C$_3$ to C$_{12}$ cycloalkylthio, C$_6$ to C$_{18}$ arylthio, C$_5$ to C$_{17}$ heteroarylthio, C$_3$ to C$_{12}$ cycloalkylalkylthio, C$_6$ to C$_{18}$ aralkylthio, C$_5$ to C$_{17}$ heteroaralkylthio, C$_1$ to C$_{18}$ alkyl-SO— or —SO$_2$, C$_3$ to C$_{12}$ cycloalkyl-SO— or —SO$_2$, C$_6$ to C$_{18}$aryl-SO— or —SO$_2$, C$_5$ to C$_{17}$ heteroaryl-SO— or —SO$_2$, C$_3$ to C$_{12}$ cycloalkylalkyl-SO— or —SO$_2$, C$_6$ to C$_{18}$ aralkyl-SO— or —SO$_2$, C$_1$ to C$_{18}$ alkyl-CO—, C$_3$ to C$_{12}$ cycloalkyl-CO—, C$_6$ to C$_{18}$aryl-CO—, C$_5$ to C$_{17}$ heteroaryl-CO—, C$_3$ to C$_{12}$ cycloalkylalkyl-CO—, C$_6$ to C$_{18}$ aralkyl-CO—, C$_5$ to C$_{17}$ heteroaralkyl-CO—, —NR$_3$R$_4$, alkoxyalkyl with 2 to 20 carbon atoms, polyoxyalkylene-OR$_6$, —X—(R$_5$)$_k$—C(O)—NR$_3$R$_4$, —X—(R$_5$)$_k$—C(O)—OR$_6$, —X—(R$_5$)$_k$—SO$_2$—OR$_6$, —X—(R$_5$)$_k$ —SO$_2$—NR$_3$R$_4$, —NH—C(O)—R$_6$ and —O—C(O)—R$_6$, wherein R$_3$ and R$_4$ independently from one another mean H, C$_1$ to C$_{20}$alkyl, cyclopentyl, cyclohexyl, phenyl, benzyl, C$_1$ to C$_{12}$alkylphenyl or C$_1$ to C$_{12}$alkylbenzyl, or R$_3$ and R$_4$ together mean tetramethylene, pentamethylene, or the groups —CH$_2$—CH$_2$—O—CH$_2$—CH$_2$— or —CH$_2$—CH$_2$—NR$_3$—CH$_2$—CH$_2$—, R$_5$ is C$_1$ to C$_{12}$alkylene, phenylene or benzylene, R$_6$ means H, C$_1$ to C$_{20}$alkyl, cyclopentyl, cyclohexyl, phenyl, benzyl, C$_1$ to C$_{12}$alkylphenyl or C$_1$ to C$_{12}$alkylbenzyl, X is a direct bond, —O— or S, k is 0 or 1 and and the salts of the acids.

Preferred salts are the alkaline metal and earth alkaline metal salts, e.g. from Li, Na, K, Mg, Ca, Sr, Ba.

The cyclic aliphatic and aromatic residues (substituents for the organic group) may be also substituted, for example with halogen like F, Cl or Br, —CN, —NO$_2$, C$_1$ to C$_{18}$alkyl, C$_3$ to C$_{12}$ cycloalkyl, C$_6$ to C$_{18}$ aryl, C$_3$ to C$_{12}$ cycloalkylalkyl, C$_6$ to C$_{18}$ aralkyl, C$_5$ to C$_{17}$ heteroaralkyl C$_1$ to C$_{18}$ alkyloxy, C$_3$ to C$_{12}$ cycloalkyloxy, C$_6$ to C$_{18}$ aryloxy.

In the context of the invention the alkyl substituent may be linear or branched and contains preferably 1 to 12 C-atoms, more preferably 1 to 8 C-atoms, most preferably 1 to 6 C-atoms and particularly preferred 1 to 4 C-atoms. Some examples are methyl, ethyl, n- or i-propyl, n-, i- or t-butyl, and the isomers of pentyl, hexyl, heptyl, octyl, nonyl, decyl, undecyl, dodecyl, tridecyl, tetradecyl, pentadecyl, hexadecyl, heptadecyl and octadecyl.

In the context of the invention the halogen substituent may be F, Cl, Br or I and is preferably F or Cl.

In the context of the invention the alkenyl substituent may be linear or branched and contains preferably 2 to 12 C-atoms, more preferably 2 to 8 C-atoms, most preferably 2 to 6 C-atoms and particularly preferred 2 to 4 C-atoms. Some examples are vinyl, allyl, methylvinyl, but-1-ene-4-yl, but-2-ene-4-yl, but-3-ene-4-yl, 3-methyl-prop-1-ene-3-yl, and the isomers of pentenyl, hexenyl, heptenyl, octenyl, nonenyl, decenyl, undeencyl, dodecenyl, tridecenyl, tetradecenyl, pentadecenyl, hexadecenyl, heptadecenyl and octadecenyl.

In the context of the invention the alkinyl substituent may be linear or branched and contains preferably 2 to 12 C-atoms, more preferably 2 to 8 C-atoms, most preferably 2 to 6 C-atoms and particularly preferred 2 to 4 C-atoms. Some examples are ethinyl, crotonyl, methylethinyl, but-1-ine-4-yl, but-2-ine-4-yl, but-3-ine-4-yl, 3-methyl-prop-1-in-3-yl, and the isomers of pentinyl, hexinyl, heptinyl, octinyl, noninyl, decinyl, undecinyl, dodecinyl, tridecinyl, tetradecinyl, pentadecinyl, hexadecinyl, heptadecinyl and octadecinyl.

In the context of the invention the hydroxyalkyl substituent may be linear or branched and contains preferably 1 to 12 C-atoms, more preferably 1 to 8 C-atoms, most preferably 1 to 6 C-atoms and particularly preferred 1 to 4 C-atoms. Some examples are hydroxymethyl, hydroxyethyl, n- or i-hydroxypropyl, n-, i- or t-hydroxybutyl, and the isomers of hydroxypentyl, hydroxyhexyl, hydroxyheptyl, hydroxyoctyl, hydroxynonyl, hydroxydecyl, hydroxyundecyl, hydroxydodecyl, hydroxytridecyl, hydroxytetradecyl, hydroxypentadecyl, hydroxyhexadecyl, hydroxyheptadecyl and hydroxyoctadecyl.

In the context of the invention the halogenalkyl substituent may be linear or branched and contains preferably 1 to 12 C-atoms, more preferably 1 to 8 C-atoms, most preferably 1 to 6 C-atoms and particularly preferred 1 to 4 C-atoms. The halogen may be F, Cl, Br or I, and is preferably F and Cl. Some examples are chloromethyl, dichloromethyl, trichloromethyl, fluoromethyl, difluoromethyl, trifluoromethyl, chloroethyl, n- or i-chloropropyl, n-, i- or t-chlorobutyl, perfluoroethyl and perfluorobutyl.

In the context of the invention the cycloalkyl substituent contains preferably 4 to 8 and more preferred 5 to 7 ring carbon atoms. Examples are cyclopropyl, cyclobutyl, cyclopentyl, cyclohexyl, cycloheptyl, cyclooctyl and cyclododecyl. Preferred groups are cyclopentyl and cyclohexyl.

In the context of the invention the aryl substituent may be naphthyl or preferably phenyl.

In the context of the invention the heteroaryl substituent contains preferably 5 or 6 ring atoms and preferably 1 to 3, more preferably 1 or 2 heteroatoms selected from the group consisting of O, S and N. Some examples are pyridinyl, pyrimidinyl, furanyl, pyrrolyl and thiophenyl.

In the context of the invention the cycloalkyl-alkyl substituent is preferably cycloalkyl-methyl or -ethyl, and cycloalkyl means preferably cyclopentyl or cyclohexyl.

In the context of the invention the aralkyl substituent is preferably arylmethyl or -ethyl, and aryl means preferably phenyl or naphthyl. Some examples are benzyl, phenylethyl and naphthylmethyl.

In the context of the invention the heteroaralkyl substituent is preferably heteroarylmethyl or -ethyl, and the heteroaryl contains preferably 5 or 6 ring atoms and preferably 1 to 3, more preferably 1 or 2 heteroatoms selected from group consisting of O, S and N. Some examples are pyridinylmethyl or -ethyl, pyrimidinyl, furanylmethyl, pyrrolylmethyl and thiophenylmethyl.

In the context of the invention the alkoxy substituent may be linear or branched and contains preferably 1 to 12 C-atoms, more preferably 1 to 8 C-atoms, most preferably 1 to 6 C-atoms and particularly preferred 1 to 4 C-atoms. Some examples are methoxy, ethoxy, n- or i-propoxy, n-, i- or t-butoxy, and the isomers of pentoxy, hexoxy, heptoxy, octoxy, nonyloxy, decyloxy, undecyloxy, dodecyloxy, tridecyloxy, tetradecyloxy, pentadecyloxy, hexadecyloxy, heptadecyloxy and octadecyloxy.

In the context of the invention the cycloalkyloxy substituent contains preferably 4 to 8 and more preferred 5 to 7 ring carbon atoms. Examples are cyclopropyloxy, cyclobutyloxy, cyclopentyloxy, cyclohexyloxy, cycloheptyloxy, cyclooctyloxy and cyclododecyloxy. Preferred groups are cyclopentyloxy and cyclohexyloxy.

In the context of the invention the aryloxy substituent may be naphthyloxy or preferably phenyloxy.

In the context of the invention the heteroaryloxy substituent contains preferably 5 or 6 ring atoms and preferably 1 to 3, more preferably 1 or 2 heteroatoms selected from group consisting of O, S and N. Some examples are pyridinyloxy, pyrimidinyloxy, furanyloxy, pyrrolyloxy and thiophenyloxy.

In the context of the invention the cycloalkyl-alkyloxy substituent is preferably cycloalkyl-methyloxy or -ethyloxy, and cycloalkyl means preferably cyclopentyl or cyclohexyl.

In the context of the invention the aralkyloxy substituent is preferably arylmethyloxy or -ethyloxy, and aryl means preferably phenyl or naphthyl. Some examples are benzyloxy, phenylethyloxy and naphthylmethyloxy.

In the context of the invention the heteroaralkyloxy substituent is preferably heteroarylmethyl or -ethyl, and the heteroaryl contains preferably 5 or 6 ring atoms and preferably 1 to 3, more preferably 1 or 2 heteroatoms selected from the group consisting of O, S and N. Some examples are pyridinylmethyloxy or -ethyloxy, pyrimidinyloxy, furanylmethyloxy, pyrrolylmethyloxy and thiophenylmethyloxy.

In the context of the invention the alkylthio substituent may be linear or branched and contains preferably 1 to 12 C-atoms, more preferably 1 to 8 C-atoms, most preferably 1 to 6 C-atoms and particularly preferred 1 to 4 C-atoms. Some examples are methylthio, ethylthio, n- or i-propylthio, n-, i- or t-butylthio, and the isomers of pentylthio, hexylthio, heptylthio, octylthio, nonylthio, decylthio, undecylthio, dodecylthio, tridecylthio, tetradecylthio, pentadecylthio, hexadecylthio, heptadecylthio and octadecylthio.

In the context of the invention the cycloalkylthio substituent contains preferably 4 to 8 and more preferred 5 to 7 ring carbon atoms. Examples are cyclopropylthio, cyclobutylthio, cyclopentylthio, cyclohexylthio, cycloheptylthio, cyclooctylthio and cyclododecylthio. Preferred groups are cyclopentylthio and cyclohexylthio.

In the context of the invention the arylthio substituent may be naphthylthio or preferably phenylthio.

In the context of the invention the heteroarylthio substituent contains preferably 5 or 6 ring atoms and preferably 1 to 3, more preferably 1 or 2 heteroatoms selected from the group consisting of O, S, N. Some examples are pyridinylthio, pyrimidinylthio, furanylthio, pyrrolylthio and thiophenylthio.

In the context of the invention the cycloalkyl-alkylthio substituent is preferably cycloalkyl-methylthio or -ethylthio, and cycloalkyl means preferably cyclopentyl or cyclohexyl.

In the context of the invention the aralkylthio substituent is preferably arylmethylthio or -ethylthio, and aryl means preferably phenyl or naphthyl. Some examples are benzylthio, phenylethylthio and naphthylmethylthio.

In the context of the invention the heteroaralkylthio substituent is preferably heteroarylmethylthio or -ethylthio, and the heteroaryl contains preferably 5 or 6 ring atoms and preferably 1 to 3, more preferably 1 or 2 heteroatoms selected from group consisting of O, S and N. Some examples are pyridinylmethylthio or -ethylthio, pyrimidinylthio, furanylmethylthio, pyrrolylmethylthio and thiophenylmethylthio.

In the context of the invention the alkyl-SO— or —SO$_2$— substituent may be linear or branched and contains preferably 1 to 12 C-atoms, more preferably 1 to 8 C-atoms, most preferably 1 to 6 C-atoms and particularly preferred 1 to 4 C-atoms. Some examples are methyl-SO— or —SO$_2$—, ethyl-SO— or —SO$_2$—, n- or i-propyl-SO— or —SO$_2$—, n-, i- or t-butyl-SO— or —SO$_2$—, and the isomers of pentyl-SO— or —SO$_2$—, hexyl-SO— or —SO$_2$—, heptyl-SO— or —SO$_2$—, octyl-SO— or —SO$_2$—, nonyl-SO— or —SO$_2$—, decyl-SO— or —SO$_2$—, undecyl-SO— or —SO$_2$—, dodecyl-SO— or —SO$_2$—, tridecyl-SO— or —SO$_2$—, tetradecyl-SO— or —SO$_2$—, pentadecyl-SO— or —SO$_2$—, hexadecyl-SO— or —SO$_2$—, heptadecyl-SO— or —SO$_2$— and octadecyl-SO— or —SO$_2$—.

In the context of the invention the cycloalkyl-SO— or —SO$_2$— substituent contains preferably 4 to 8 and more preferred 5 to 7 ring carbon atoms. Examples are cyclopropyl-SO— or —SO$_2$—, cyclobutyl-SO— or —SO$_2$—, cyclopentyl-SO— or —SO$_2$—, cyclohexyl-SO— or —SO$_2$— cycloheptyl-SO— or —SO$_2$—, cyclooctyl-SO— or —SO$_2$— and cyclododecyl-SO— or —SO$_2$—. Preferred groups are cyclopentyl-SO— or —SO$_2$— and cyclohexyl-SO— or SO$_2$—.

In the context of the invention the aryl-SO— or —SO$_2$— substituent may be naphthyl-SO— or —SO$_2$— or preferably phenyl-SO— or —SO$_2$—.

In the context of the invention the heteroaryl-SO— or —SO$_2$— substituent contains preferably 5 or 6 ring atoms and preferably 1 to 3, more preferably 1 or 2 heteroatoms selected from the group consisting of O, S and N. Some examples are pyridinyl-SO— or —SO$_2$—, pyrimidinyl-SO— or —SO$_2$—, furanyl-SO— or —SO$_2$—, pyrrolyl-SO— or —SO$_2$— and thiophenyl-SO— or —SO$_2$—.

In the context of the invention the cycloalkyl-alkyl-SO— or —SO$_2$— substituent is preferably cycloalkyl-methyl-SO— or —SO$_2$— or -ethyl-SO— or —SO$_2$—, and cycloalkyl means preferably cyclopentyl or cyclohexyl.

In the context of the invention the aralkyl-SO— or —SO$_2$— substituent is preferably arylmethyl-SO— or —SO$_2$— or -ethyl-SO— or —SO$_2$—, and aryl means preferably phenyl-SO— or —SO$_2$— or naphthyl-SO— or —SO$_2$—. Some examples are benzyl-SO— or —SO$_2$—, phenylethyl-SO— or —SO$_2$— and naphthylmethyl-SO— or —SO$_2$—.

In the context of the invention the heteroaralkyl-SO— or —SO$_2$— substituent is preferably heteroarylmethyl-SO— or —SO$_2$— or -ethyl-SO— or —SO$_2$—, and the heteroaryl contains preferably 5 or 6 ring atoms and preferably 1 to 3, more preferably 1 or 2 heteroatoms selected from the group consisting of O, S and N. Some examples are pyridinylmethyl-SO— or —SO$_2$— or -ethyl-SO— or —SO$_2$—, pyrimidinyl-SO— or —SO$_2$—, furanylmethyl-SO— or —SO$_2$—, pyrrolylmethyl-SO— or —SO$_2$— and thiophenylmethyl-SO— or —SO$_2$—.

In the context of the invention the alkyl-CO— substituent may be linear or branched and contains preferably 1 to 12 C-atoms, more preferably 1 to 8 C-atoms, most preferably 1 to 6 C-atoms and particularly preferred 1 to 4 C-atoms. Some examples are methyl-CO—, ethyl-CO—, n- or i-propyl-CO—, n-, i- or t-butyl-CO—, and the isomers of pentyl-CO—, hexyl-CO—, heptyl-CO—, octyl-CO—, nonyl-CO—, decyl-CO—, undecyl-CO—, dodecyl-CO—, tridecyl-CO—, tetradecyl-CO—, pentadecyl-CO—, hexadecyl-CO—, heptadecyl-CO— and octadecyl-CO—.

In the context of the invention the cycloalkyl-CO— substituent contains preferably 4 to 8 and more preferred 5 to 7 ring carbon atoms. Examples are cyclopropyl-CO—, cyclobutyl-CO—, cyclopentyl-CO—, cyclohexyl-CO—, cycloheptyl-CO—, cyclooctyl-CO— and cyclododecyl-CO—. Preferred groups are cyclopentyl-CO— and cyclohexyl-CO—.

In the context of the invention the aryl-CO— substituent may be naphthyl-CO— or preferably phenyl-CO—.

In the context of the invention the heteroaryl substituent contains preferably 5 or 6 ring atoms and preferably 1 to 3, more preferably 1 or 2 heteroatoms selected from group consisting of O, S and N. Some examples are pyridinyl, pyrimidinyl, furanyl, pyrrolyl and thiophenyl.

In the context of the invention the cycloalkyl-alkyl-CO— substituent is preferably cycloalkylmethyl-CO— or -ethyl-CO—, and cycloalkyl means preferably cyclopentyl or cyclohexyl.

In the context of the invention the aralkyl-CO— substituent is preferably arylmethyl-CO— or -ethyl-CO—, and aryl means preferably phenyl-CO— or naphthyl-CO—. Some examples are benzyl-CO—, phenylethyl-CO— and naphthylmethyl-CO—.

In the context of the invention the heteroaralkyl-CO— substituent is preferably hetero-arylmethyl-CO— or -ethyl-CO—, and the heteroaryl contains preferably 5 or 6 ring atoms and preferably 1 to 3, more preferably 1 or 2 heteroatoms selected from group consisting of O, S and N. Some examples are pyridinylmethyl-CO— or -ethyl-CO—, pyrimidinyl-CO—, furanylmethyl-CO—, pyrrolylmethyl-CO— and thiophenylmethyl-CO—.

In the context of the invention the alkoxyalkyl substituent contains preferably in total 2 to 12, more preferably 2 to 8 and most preferably 2 to 6 carbon atoms. The alkoxy may contain 1 to 4 carbon atoms. Some examples are methoxyethyl, methoxyethyl, methoxypropyl, methoxybutyl, methoxypentyl, methoxyhexyl, ethoxymethyl, ethoxyethyl, ethoxypropyl, ethoxybutyl, ethoxypentyl, ethoxyhexyl, propoxymethyl and butoxymethyl.

In the context of the invention the polyoxyalkylene-O—R$_6$ substituent preferably contains 2 to 12 and more preferably 2 to 6 oxyalkylene units, wherein alkylene is preferably ethylene, 1,2- or 1,3-propylene or 1,2-1,3- or 1,4-butylene. R$_6$ is preferably H or C$_1$ to C$_4$alkyl.

In the context of the invention R$_3$ and R$_4$ in the meaning of alkyl may be linear or branched and contain preferably 1 to 12 C-atoms, more preferably 1 to 8 C-atoms, most preferably 1 to 6 C-atoms and particularly preferred 1 to 4 C-atoms. Some examples are methyl, ethyl, n- or i-propyl, n-, i- or t-butyl, and the isomers of pentyl, hexyl, heptyl, octyl, nonyl, decyl, undecyl, dodecyl, tridecyl, tetradecyl, pentadecyl, hexadecyl, heptadecyl and octadecyl.

In the context of the invention $R_3$ and $R_4$ in the meaning of alkylphenyl may be preferably $C_1$ to $C_8$alkylphenyl, $C_1$ to $C_4$alkylphenyl. Some examples are methylbenzyl, ethylphenyl, n- or i-propylphenyl, n-, i- or t-butylphenyl, hexylphenyl, octylphenyl, dodecylphenyl, and dimethylphenyl.

In the context of the invention $R_3$ and $R_4$ in the meaning of alkylbenzyl may be preferably $C_1$ to $C_8$alkylbenzyl, $C_1$ to $C_4$alkylbenzyl. Some examples are methylbenzyl, ethylbenzyl, n- or i-propylbenzyl, n-, i- or t-butylbenzyl, hexylbenzyl, octylbenzyl, dodecylbenzyl, and dimethyl benzyl.

In the context of the invention $R_3$ and $R_4$ mean independently from one another preferably H, $C_1$ to $C_4$alkyl, cyclohexyl, phenyl, benzyl, $C_1$ to $C_4$alkylphenyl or $C_1$ to $C_4$alkylbenzyl, or $R_3$ and $R_4$ together mean tetramethylene, pentamethylene, or the group —$CH_2$—$CH_2$—O—$CH_2$—$CH_2$—.

In the context of the invention $R_5$ in the meaning of alkylene is preferably $C_1$ to $C_6$alkylene, $C_1$ to $C_4$alkylene, for example methylene, ethylene, propylene or butylene. Most preferred $R_5$ is methylene, ethylene, phenylene or benzylene.

In the context of the invention wherein $R_6$ is alkyl, it may be linear or branched and contain preferably 1 to 12 C-atoms, more preferably 1 to 8 C-atoms, most preferably 1 to 6 C-atoms and particularly preferred 1 to 4 C-atoms. Some examples are methyl, ethyl, n- or i-propyl, n-, i- or t-butyl, and the isomers of pentyl, hexyl, heptyl, octyl, nonyl, decyl, undecyl, dodecyl, tridecyl, tetradecyl, pentadecyl, hexadecyl, heptadecyl and octadecyl. $R_6$ is preferably H, $C_1$ to $C_{12}$alkyl, cyclopentyl, cyclohexyl, phenyl, benzyl.

Examples for substituents are F, Cl, Br, methyl, ethyl, propyl, butyl, hexyl, methyloxy, ethyloxy, propyloxy, butyloxy, hexyloxy, methylthio, ethylthio, methyl- or ethyl-SO—, methyl- or ethyl-$SO_2$—, phenyl, benzyl, toluyl, xylyl, methylbenzyl, dimethylbenzyl, chlorophenyl, dichlorophenyl, methoxyphenyl, dimethoxyphenyl, methoxybenzyl, dimethoxybenzyl, $CH_3$—CO—, $C_6H_5$—CO—, $CH_3$—CO—O—, $C_6H_5$—CO—O—, $CH_3$—$SO_2$—O—, $C_6H_5$—$SO_2$—O—, —$NH_2$, —$NHCH_3$, —$NHC_2H_5$, $NHC_8H_{17}$, —$N(CH_3)_2$, —COOH, —CO—$OCH_3$, —CO—$OC_2H_5$, $SO_3H$, —$SO_2$—$OCH_3$, $SO_2$—$OC_2H_5$, —CO—$NH_2$, —CO—$NCH_3$, —CO—$NHC_2H_5$, —CO—$NHC_8H_{17}$, —CO—$NH(CH_3)_2$, —$SO_2$—$NH_2$, —$SO_2$—$NHCH_3$, —$SO_2$—$NHC_2H_5$, —$SO_2$—$NHC_8H_{17}$, —$SO_2$—$N(CH_3)_2$, $H_2N$—$SO_2$—, methoxymethyl, methoxyethyl, ethoxyethyl, —$(OCH_2CH_2)_2$—OH, —CN and —$NO_2$.

The number of substituents is arbitrary and depends essentially upon synthetic possibilities, the desired optical properties related to fluorescence and absorption, and the desired solubility.

In a preferred embodiment of the invention the compounds of formula I correspond to formula II,

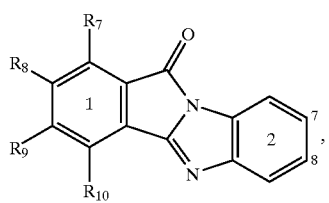

(II)

wherein
$R_7$, $R_8$, $R_9$ and $R_{10}$ independently from one another can be H, F, Cl, Br, I, $C_1$ to $C_{18}$alkyl, $C_1$ to $C_{18}$alkoxy, $C_1$ to $C_{18}$alkylthio, aryl, aralkyl, $C_1$ to $C_{12}$alkyl-aryl or $C_1$ to $C_{12}$ alkyl-aralkyl, and the ring 2 is unsubstituted or substituted as described before, including the preferred substituents.

Preferably at least one of $R_7$, $R_8$, $R_9$ and $R_{10}$ is one of the defined substituents. More preferably $R_8$ and $R_9$ are one of the defined substituents. Mostly preferred $R_7$, $R_8$, $R_9$ and $R_{10}$ are substituents.

In the context of the invention when $R_7$, $R_8$, $R_9$ and $R_{10}$ mean linear alkyl or branched alkyl they contain preferably 1 to 12 C-atoms, more preferably 1 to 8 C-atoms, most preferably 1 to 6 C-atoms and particularly preferred 1 to 4 C-atoms. Some examples are methyl, ethyl, n- or i-propyl, n-, i- or t-butyl, and the isomers of pentyl, hexyl, heptyl, octyl, nonyl, decyl, undecyl, dodecyl, tridecyl, tetradecyl, pentadecyl, hexadecyl, heptadecyl and octadecyl.

In the context of the invention when $R_7$, $R_8$, $R_9$ and $R_{10}$ mean linear alkoxy or alkoxy branched they contain preferably 1 to 12 C-atoms, more preferably 1 to 8 C-atoms, most preferably 1 to 6 C-atoms and particularly preferred 1 to 4 C-atoms. Some examples are methoxy, ethoxy, n- or i-propoxy, n-, i- or t-butoxy, and the isomers of pentoxy, hexoxy, heptoxy, octoxy, nonyloxy, decyloxy, undecyloxy, dodecyloxy, tridecyloxy, tetradecyloxy, pentadecyloxy, hexadecyloxy, heptadecyloxy and octadecyloxy.

In the context of the invention when $R_7$, $R_8$, $R_9$ and $R_{10}$ mean linear alkylthio or alkylthio branched they contain preferably 1 to 12 C-atoms, more preferably 1 to 8 C-atoms, most preferably 1 to 6 C-atoms and particularly preferred 1 to 4 C-atoms. Some examples are methylthio, ethylthio, n- or i-propylthio, n-, i- or t-butylthio, and the isomers of pentylthio, hexylthio, heptylthio, octylthio, nonylthio, decylthio, undecylthio, dodecylthio, tridecylthio, tetradecylthio, pentadecylthio, hexadecylthio, heptadecylthio and octadecylthio.

In the context of the invention $R_7$, $R_8$, $R_9$ and $R_{10}$ may be aryl naphthyl or preferably phenyl.

In the context of the invention $R_7$, $R_8$, $R_9$ and $R_{10}$ may be aralkyl preferably arylmethyl or -ethyl, wherein aryl means preferably phenyl or naphthyl. Some examples are benzyl, phenylethyl and naphthylmethyl.

In the context of the invention when $R_7$, $R_8$, $R_9$ and $R_{10}$ are alkyl-aryl they are preferably alkylphenyl, more preferably $C_1$ to $C_8$alkylphenyl, and most preferably $C_1$ to $C_4$alkylphenyl. Some examples are methylphenyl, ethylphenyl, n- or i-propylphenyl, n-, i- or t-butylphenyl, hexylphenyl, octylphenyl, dodecylphenyl, and dimethylphenyl.

In the context of the invention when $R_7$, $R_8$, $R_9$ and $R_{10}$ are alkyl-aralkyl they are preferably alkyl-benzyl, more preferably $C_1$ to $C_8$alkylbenzyl, and most preferably $C_1$ to $C_4$alkylbenzyl.

Some examples are methylbenzyl, ethylbenzyl, n- or i-propylbenzyl, n-, i- or t-butylbenzyl, hexylbenzyl, octylbenzyl, dodecylbenzyl, and dimethylbenzyl.

In an especially preferred embodiment of the invention the ring 2 is also substituted, particularly in the 7-position, in the 8-position or in both with in organic group substituent.

In a particularly preferred embodiment of the invention the compounds of formula II corresponds to formula III, (III)

[Chemical structure diagram showing a fused ring system with substituents R7, R8, R9, R10 on ring 1 and R11, R12 on ring 2, with a carbonyl group and nitrogen atoms]

wherein
- $R_7$, $R_8$, $R_9$ and $R_{10}$ are Cl, phenyl or $C_1$ to $C_{12}$alkylphenyl,
- $R_{11}$ is H or an organic group substituent, and
- $R_{12}$ is H or an organic group substituent.

The ring 2 is preferably monosubstituted, meaning that one of $R_{11}$ and $R_{12}$ is an organic group substituent.

Particularly preferred $R_7$, $R_8$, $R_9$ and $R_{10}$ are chlorine or phenyl.

In the context of the invention when $R_{11}$ or $R_{12}$ organic group substituents they are preferably selected from the group consisting of —CN, —$NO_2$, —COOH, $C_1$ to $C_{18}$ alkyl, $C_2$ to $C_{18}$alkenyl, $C_2$ to $C_{18}$alkinyl, $C_1$ to $C_{18}$ hydroxyalkyl, $C_1$ to $C_{18}$ halogenalkyl, $C_3$ to $C_{12}$ cycloalkyl, $C_6$ to $C_{18}$ aryl, $C_3$ to $C_{12}$ cycloalkyl-alkyl, $C_6$ to $C_{18}$ aralkyl, $C_1$ to $C_{18}$ alkyloxy, $C_3$ to $C_{12}$ cycloalkyloxy, $C_6$ to $C_{18}$ aryloxy, $C_3$ to $C_{12}$ cycloalkyl-alkyloxy, $C_6$ to $C_{18}$ aralkyloxy, $C_1$ to $C_{18}$ alkylthio, $C_3$ to $C_{12}$ cycloalkylthio, $C_6$ to $C_{18}$ arylthio, $C_3$ to $C_{12}$ cycloalkyl-alkylthio, $C_6$ to $C_{18}$ aralkylthio, $C_1$ to $C_{18}$ alkyl-CO—, $C_3$ to $C_{12}$ cycloalkyl-CO—, $C_6$ to $C_{18}$aryl-CO—, $C_3$ to $C_{12}$ cycloalkylalkyl-CO—, $C_6$ to $C_{18}$ aralkyl-CO—, —$NR_3R_4$, alkoxyalkyl with 2 to 20 carbon atoms, polyoxyalkylene-$OR_6$, —X—$(R_5)_k$—C(O)—$NR_3R_4$, —X—$(R_5)_k$—C(O)—$OR_6$, —X—$(R_5)_k$—$SO_2$—$OR_6$, —X—$(R_5)_k$—$SO_2$—$NR_3R_4$, —NH—C(O)—$R_6$ and —O—C(O)—$R_6$, wherein
- $R_3$ and $R_4$ independently from one another can be H, $C_1$ to $C_{20}$alkyl, cyclopentyl, cyclohexyl, phenyl, benzyl, $C_1$ to $C_{12}$alkylphenyl or $C_1$ to $C_{12}$alkylbenzyl, or $R_3$ and $R_4$ together mean tetramethylene, pentamethylene, or the groups —$CH_2$—$CH_2$—O—$CH_2$—$CH_2$— or —$CH_2$—$CH_2$—$NR_3$—$CH_2$—$CH_2$—,
- $R_5$ is $C_1$ to $C_{12}$alkylene, phenylene or benzylene,
- $R_6$ means H, $C_1$ to $C_{20}$alkyl, cyclopentyl, cyclohexyl, phenyl, benzyl, $C_1$ to $C_{12}$alkylphenyl or $C_1$ to $C_{12}$alkylbenzyl,
- X is a direct bond, —O— or S,
- k is 0 or 1 and and the salts of the acids.

The preferred meanings described before are also valid for the meanings of $R_{11}$, $R_{12}$, X and $R_3$ to $R_6$, when $R_{11}$ and $R_{12}$ are organic group substituents they are most preferably selected from the group consisting of —CN, —$NO_2$, $C_1$ to $C_{18}$ alkyl, $C_1$ to $C_{18}$ hydroxyalkyl, $C_5$ to $C_7$ cycloalkyl, $C_6$ to $C_{10}$ aryl, $C_7$ to $C_{11}$ aralkyl, $C_1$ to $C_{18}$ alkyloxy, $C_3$ to $C_{12}$ cycloalkyloxy, $C_6$ to $C_{10}$ aryloxy, $C_5$ to $C_7$ cycloalkyl-alkyloxy, $C_7$ to $C_{11}$ aralkyloxy, $C_1$ to $C_{18}$ alkylthio, $C_5$ to $C_7$ cycloalkylthio, $C_6$ to $C_{10}$ arylthio, $C_5$ to $C_7$ cycloalkyl-alkylthio, $C_7$ to $C_{11}$ aralkylthio, $C_1$ to $C_1$ alkyl-CO—, $C_5$ to $C_7$ cycloalkyl-CO—, $C_6$ to $C_{10}$aryl-CO—, $C_5$ to $C_7$ cycloalkyl-alkyl-CO—, $C_7$ to $C_{11}$ aralkyl-CO—, —$NR_3R_4$, alkoxyalkyl with 2 to 12 carbon atoms, polyoxyalkylene-$OR_6$, —X—$(R_5)_k$—C(O)—$NR_3R_4$, —X—$(R_5)_k$—C(O)—$OR_6$, —X—$(R_5)_k$—$SO_2$—$OR_6$, —X—$(R_5)_k$—$SO_2$—$NR_3R_4$, —NH—C(O)—$R_6$ and —O—C(O)—$R_6$, wherein
- $R_3$ and $R_4$ independently from one another mean H, $C_1$ to $C_6$alkyl, cyclopentyl, cyclohexyl, phenyl, benzyl, $C_1$ to $C_6$alkylphenyl or $C_1$ to $C_6$alkylbenzyl, or $R_3$ and $R_4$ together mean tetramethylene, pentamethylene, or the group —$CH_2$—$CH_2$—O—$CH_2$—$CH_2$—,
- $R_5$ is $C_1$ to $C_4$alkylene, phenylene or benzylene,
- $R_6$ means H, $C_1$ to $C_{12}$alkyl, cyclopentyl, cyclohexyl, phenyl, benzyl, $C_1$ to $C_6$alkylphenyl or $C_1$ to $C_6$alkylbenzyl,
- X is a direct bond, —O— or S,
- k is 0 or 1 and and the salts of the acids.

In an especially preferred embodiment of the invention $R_{11}$ and $R_{12}$ are selected from the group consisting of —$NO_2$, $C_1$ to $C_{18}$ alkyl, which is linear or branched, $C_1$ to $C_{18}$ alkyloxy, which is linear or branched, —C(O)OH, or —C(O)—O—$C_1$ to $C_{18}$alkyl.

The compounds of formula I to III are partially known or can be easily prepared from unsubstituted or substituted orthophenylenediamines and from unsubstituted or substituted phthalic anhydride as for example described in EP-A-0 456 609.

The guest chromophore can be selected from a broad range of pigments, pigment derivatives, dyes and their derivatives and mixtures thereof, so long as they are luminescent in the molecular state, and their absorption spectra do overlap with the emission spectrum of the host chromophore. Some guest chromophores are for example described in WO 93/23492.

In one embodiment of this invention, the guest chromophore preferably is soluble, at least to some extent, in a solvent, and—if desired—in the host chromophore, allowing formation of homogeneous solid solutions.

Solubility of a guest chromophore means in the context of the invention that at least 200 mg, more preferably at least 300 mg and most preferably at least 500 mg of the guest chromophore are soluble in 1 liter of solvent like dimethylformamide at 20° C. This definition employs also to compositions where the host and guest chromophores are embedded in a polymer matrix.

The guest chromophore may be selected from the group consisting of quinacridones, perylenes, perinones, diketo- and dithioketopyrrolopyrroles, rhodamines, coumarins, xanthens, oxazines, oxazoles, cyanines, phthalocyanines, porphyrines, styryl dyes, metal complexes and mixtures thereof.

Preferred guest chromophores are selected from group consisting of quinacridones, perylenes, perinones, diketopyrrolopyrroles, rhodamines, coumarins, cyanines, phthalocyanines, porphyrines, styryl dyes and mixtures thereof. Especially preferred are quinacridones, perylenes, diketopyrrolopyrroles, rhodamines, coumarins and mixtures thereof.

The guest compounds and their derivatives are well known in the art or can be prepared by analogous processes.

Quinacridones can be found described in Chemical Reviews 67 (1) pages 1 to 18 (1967).

The quinacridones may correspond to the formula VII

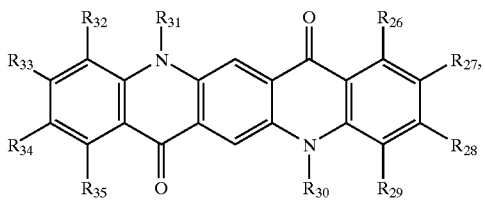

(VII)

wherein
$R_{26}$ to $R_{29}$ and $R_{32}$ to $R_{35}$ independently from one another can be H, $C_1$ to $C_6$alkyl, $C_1$ to $C_6$alkoxy, F, Cl, Br, CN, $NO_2$, or $-NR_{21}R_{22}$, wherein $R_{21}$ and $R_{22}$ independently from one another are H, $C_1$ to $C_{20}$alkyl, phenyl, $C_1$ to $C_{12}$alkylphenyl, benzyl or $C_1$ to $C_{12}$alkylbenzyl, or $R_{21}$ and $R_{22}$ together mean tetramethylene, pentamethylene or $-CH_2CH_2-O-CH_2CH_2-$; or two neighbored residues of $R_{26}$ to $R_{29}$ and/or $R_{32}$ to $R_{35}$ together with carbon atoms, to which they are linked, a 5- or 6-membered aliphatic, heteroaliphatic, aromatic or heteroaromatic ring, whereby the heteroatoms are selected from the group of $-O-$, $-S-$ and N; and $R_{30}$ and $R_{31}$ independently from one another are H, $C_1$ to $C_{18}$alkyl, $C_2$ to $C_{18}$alkenyl, $C_2$ to $C_{18}$alkinyl, phenyl, benzyl, $C_1$ to $C_6$alkylphenyl, $C_1$ to $C_6$alkylbenzyl or $R_{36}-O-C(O)-$, wherein $R_{36}$ means $C_1$ to $C_{18}$alkyl, $C_2$ to $C_{18}$alkenyl, $C_2$ to $C_{18}$alkinyl, phenyl, benzyl, $C_1$ to $C_6$alkylphenyl, or $C_1$ to $C_6$alkylbenzyl.

Perylenes can be found described in U.S. Pat. Nos. 4,446,324 and 5,470,502. Preferred examples are those perylenes of formulae IX and X,

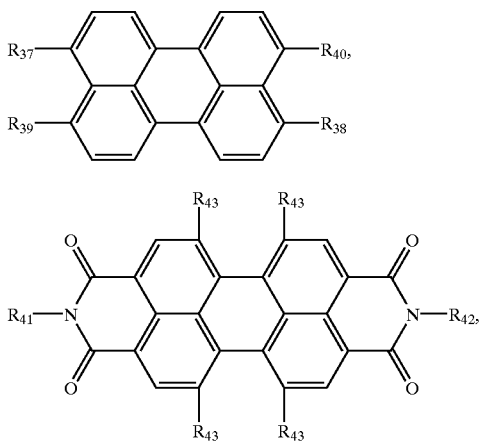

(IX)

(X)

wherein
$R_{37}$ and $R_{38}$ independently from one another can be F, Cl, Br, or CN,
$R_{39}$ and $R_{40}$ independently from one another mean $R_{36}-O-C(O)-$, wherein $R_{36}$ means $C_1$ to $C_{18}$alkyl, $C_2$ to $C_{18}$alkenyl, $C_2$ to $C_{18}$alkinyl, phenyl, benzyl, $C_1$ to $C_6$alkyl phenyl, or $C_1$ to $C_6$alkylbenzyl.
$R_{41}$ and $R_{42}$ independently from one another can be H, $C_1$ to $C_{18}$alkyl, $C_2$ to $C_{18}$alkenyl, $C_2$ to $C_{18}$alkinyl, phenyl, benzyl, $C_1$ to $C_6$alkylphenyl, $C_1$ to $C_6$alkylbenzyl or $R_{36}-O-C(O)-$, wherein $R_{36}$ means $C_1$ to $C_{18}$alkyl, $C_2$ to $C_{18}$alkenyl, $C_2$ to $C_{18}$alkinyl, phenyl, benzyl, $C_1$ to $C_6$alkylphenyl, or $C_1$ to $C_6$alkyl benzyl, and the $R_{43}$ independently from one another are $C_1$ to $C_{18}$alkoxy, phenoxy or $C_1$ to $C_{12}$alkyl-phenoxy.

Some examples are the commercially available compounds are shown;

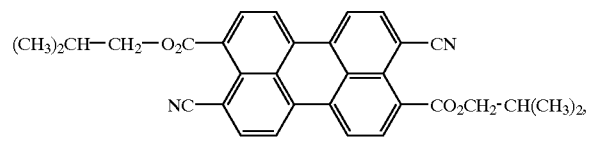

(Lumogen F Yellow)

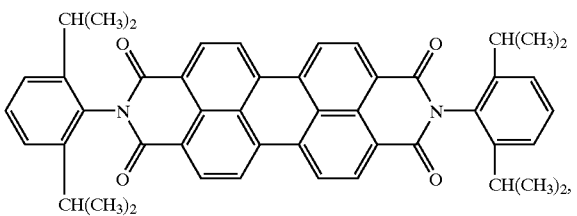

(Lumogen F Orange)

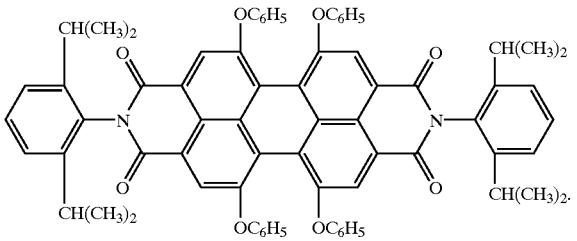

(Lumogen F Red)

Diketo- and dithioketopyrrolopyrroles can be found described in U.S. Pat. No. 4,415,685 and JP-A-61 162 555.

Examples for diketopyrrolopyrroles correspond to the formula XI,

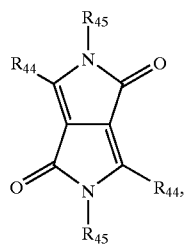

(XI)

wherein
the $R_{44}$ independently from one another are H, halogen, or phenyl which is unsubstituted or substituted with $C_1$ to $C_6$alkyl, $C_1$ to $C_6$alkoxy, phenyl, $C_1$ to $C_4$alkylphenyl, F, Cl, Br, CN, $NO_2$, or $-NR_{21}R_{22}$, wherein $R_{21}$ and $R_{22}$ independently from one another are H, $C_1$ to $C_{20}$alkyl, phenyl, $C_1$ to $C_{12}$alkylphenyl, benzyl or $C_1$ to $C_{12}$alkylbenzyl, or $R_{21}$ and $R_{22}$ together mean tetramethylene, pentamethylene or $-CH_2CH_2-O-CH_2CH_2-$; and
the $R_{45}$ independently from one another mean H, $C_1$ to $C_{18}$alkyl, $C_2$ to $C_{18}$alkenyl, $C_2$ to $C_{18}$alkinyl, phenyl, benzyl, $C_1$ to $C_6$alkyl phenyl, or $C_1$ to $C_6$alkylbenzyl, or $R_{30}-O-C(O)-$, wherein
$R_{30}$ means $C_1$ to $C_{18}$alkyl, $C_2$ to $C_{18}$alkenyl, $C_2$ to $C_{18}$alkinyl, phenyl, benzyl, $C_1$ to $C_6$alkylphenyl, or $C_1$ to $C_6$alkyl benzyl.

A range of commercial rhodamines are available from ACROS ORGANICS catalogue of fine chemicals Vol. 1 (1996).

Preferred examples of rhodamines are those of the formula XII,

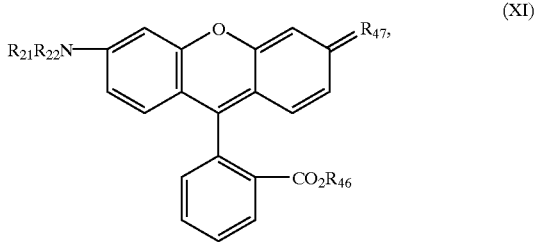

(XI)

wherein
wherein $R_{21}$ and $R_{22}$ independently from one another are H, $C_1$ to $C_{20}$alkyl, phenyl, $C_1$ to $C_{12}$alkylphenyl, benzyl or $C_1$ to $C_{12}$alkylbenzyl, or $R_{21}$ and $R_{22}$ together mean tetramethylene, pentamethylene or —$CH_2CH_2$—O—$CH_2CH_2$—;

$R_{46}$ means H, $C_1$ to $C_{18}$alkyl, $C_2$ to $C_{18}$alkenyl, $C_2$ to $C_{18}$alkinyl, phenyl, benzyl, $C_1$ to $C_6$alkyl phenyl, or $C_1$ to $C_6$alkylbenzyl, or an equivalent of a metal or ammonium cation;

and $R_{47}$ means the group =$NR_{48}$, or the group =$^+NR_{48}R_{49}X^-$, $R_{48}$ and $R_{49}$ independently from one another are H, $C_1$ to $C_{18}$alkyl, phenyl, $C_1$ to $C_{12}$alkylphenyl, benzyl or $C_1$ to $C_{12}$alkylbenzyl; and X is monovalent anion.

A range of commercial coumarins, oxazines, cyanines, xanthens and styryl dyes are available from ACROS ORGANICS catalogue of fine chemicals Vol. 1 (1996). A range of commercial oxazoles are available from DOJINDO LABORATORIES catalogue 18th edition (1992).

Porphyrines and phthalocyanines are for example described in a book "The Phthalocyanines" (Frank H. Moser et. al., published by Franklin, 1983).

In the context of the invention, effective amount of a guest chromophore means for example, that the composition may contain from 0.001 to 30, preferably from 0.01 to 20, more preferably from 0.01 to 10 and most preferably from 0.01 to 5 percent by weight, of guest chromophore, related to the total amount of host and guest chromophore.

Further, in the context of this invention, the meaning of the overlap of the absorption spectrum of the guest chromophore with the fluorescence emission spectrum of the host chromophore, is clear to a skilled person in this field. However, to facilitate the understanding to others, overlap means "spectral overlap" defined by the following integral $$S = \int_0^{+\infty} f_F(v) f_A(v) dv$$

wherein $f_F(v)$ is normalized, so that $$\int_0^{+\infty} f_F(v) dv$$

is equal to fluorescence quantum yield of the host, and where v is the wave number, $f_F$ the fluorescence spectrum of the host measured in quanta, and $f_A$ the spectral distribution of the molar extinction coefficient of the guest. The spectral overlap to realize photoluminescence enhancement usually is greater than 10, preferably greater than 100, more preferably greater than 500. An upper limit makes no sense, because the quantity "overlap" has no maximum (i.e. the larger, the better)).

In the context of this invention, embedded means a distribution of the guest chromophore (or both host and guest chromophore, if a polymer matrix is used) within the matrix or total amount of host chromophore (or— accordingly, of course, the polymer matrix). Preferably, this distribution is homogeneously. Hence, in another preferred embodiment of this invention, (a) the guest chromophore is homogeneously distributed within the matrix of the host chromophore, or (b) the host chromophore and the guest chromophore both are homogeneously distributed within the polymer matrix.

In the context of this invention, the term "homogeneously" means that the components within the matrix, e.g. the guest chromophore, is evenly or uniformly distributed or dispersed throughout the matrix (or host or host/polymer matrix), and, preferably in the ideal case are essentially equidistant from each other. According to observations today, the more even or uniform the distribution is, the better are the fluorescence properties, because the coexistence of areas having bright and weak fluorescence are reduced as well as areas wherein the emission color is closer to that of the host than the guest. Furthermore, a homogeneous or even distribution is preferred, because usually the chances for aggregation are decreased.

In another preferred embodiment of this invention, the average particle size of the guest chromophores (or the host and guest chromophores, if a polymer matrix is applied) are not bigger than a desired diameter, preferably more than a desired amount of the guest chromophores (or host and guest chromophores, if a polymer matrix is applied) are in their molecular state. Most preferably, the guest chromophores (or host and guest chromophores, if a polymer matrix is applied) are molecularly dissolved and homogeneously distributed within the matrix of the host chromophore (or the polymer matrix).

In the context of this invention, the term "dissolved" means that a molecule exists as a free and isolated entity in a given matrix, preferably in such a way, that it is disengaged from any interactions between molecules of the same species, i.e. it is entirely surrounded by matrix molecules. Usually the matrix can be a liquid organic solvent or a solid material such as a polymer or another fluorescent material (host), which possesses a different chemical structure. The concentration limits for molecules in the dissolved state in general depend strongly on the associative nature between the molecule and the matrix medium, and/or the intrinsic cohesive forces that exist between the guest molecules in question. Correspondingly, it is impossible to define universal ranges for preferred concentrations, and therefore, usually must be treated on an ad hoc basis, e.g. by a few simple experiments.

Polymers which may be used as polymer matrix may be selected from thermoplastics, polymer blends, thermosettings and structurally crosslinked polymers. The polymers may be homopolymers, copolymers, blockpolymers, graft polymers or random polymers.

The polymers may be opaque or translucent but preferably transparent. The polymers may be selected for example from the group of thermoplastic polymers like polyesters, poly amides, polyimides, polyamide-imides, polyamide esters, polyurethanes, polyureas, polyolefines; polymers from substituted olefines like vinylethers, vinylesters, vinylalcohols, vinylchloride, vinyldichloride, acetonitrile, acrylic acid, methacrylic acid, esters and amides of acrylic acid and methacrylic acid, styrene, chlorostyrene, methylstyrene, styrene sulfonic acid and their esters and amides, vinylcarbazole, vinylpyridine, vinylpyrrolidone: polymaleic acid and esters and amides therefrom; polyethers (for example from bisphenol-A diglycidyl ether), polysulfones, polyketones, polyphenylsulfides, and polyacetales; and natural polymers and their derivatives like cellulose and its esters and ethers, and starch or derivatives of starch.

Examples of thermosetting resins and structurally crosslinked resins are polyepoxides, unsaturated polyesters, photocrosslinked resins for example from acrylic acid and/or methacrylic esters and/or amides from polyols and/or polyamines, melamine/formaldehyde resins, and phenol/formaldehyde resins; polymers from butadiene, isoprene and or chloroprene and copolymers with olefins, which may be crosslinked and of rubbery nature, including latices; as well as silicates obtainable through the known sol/gel process.

The polymeric compositions of the invention may contain further ingredients to enhance certain features such as electrical, physical and mechanical properties, and/or the processability, for example dispersing agents to achieve a uniform distribution of particles, lubricants, plasticizers, antistatica, solvents, molding agents, antioxidants, light stabilizers, fillers and reinforcing fillers like glass balls and glass fibers, silicates (e.g. mica, clay, wollastonite), metal and semiconductor metal oxides, metal carbonates, metal salts, metals and semiconductor metals, carbon black, as powder, or carbon fibers, whiskers, metal and semiconductor metal carbides, metal and semiconductor metal nitrides, dyes, pigments and others.

The weight ratio of (host chromophores plus guest chromophores):polymer matrix is dependent on the actual practical application, hence there are no well defined preferred ratios, other than the broad range 99:1 to 1:999. In certain applications where both color strength and fluorescence are required, then the preferred ratios of the chromophores to the polymer matrix are 20:80 to 99:1, preferably 50:50 to 99:1 and more preferably 80:20 to 99:1. In circumstances where fluorescence is desired but color strength is not required, then the preferred ratio of the chromophores to the polymer matrix are 20:80 to 1:999, more preferably 10:90 to 1:999 and more preferably 5:95 to 1:999.

The composition according to the invention can be prepared using known processes like co-sublimation, as described in JP-A-03 255 190, or new processes that utilize the solubility of the guest chromophores.

A further embodiment of the invention is a process for the preparation of the inventive, abovementioned composition, comprising a host chromophore and a guest chromophore and, if desired, a polymer matrix, wherein the absorption spectrum of the guest chromophore overlaps with the fluorescence emission spectrum of the host chromophore, characterized in
(a) selecting the host chromophore from the group consisting of benzo[4,5]imidazo[2,1-a]isoindol-11-ones,
(b) mixing the host chromophore and an effective amount of at least one guest chromophore, and optionally a polymer or polymerisable precursor, in the presence of a solvent, and
c) then precipitating the host and guest chromophores, optionally in the presence the polymer of step (b), or (d) precipitating the host and guest chromophores during polymerization of the polymer precursor of step (b).

In the context of the invention mixing of the materials can be achieved through dissolution of the components in a common solvent and followed by the subsequent evaporation of the solvent; precipitation from a good solvent into a poor solvent (vigorous stirring can be applied); freeze-drying; and precipitation during polymerization of polymerizable monomers or oligomers, preferably under vigorous stirring.

Suitable inert solvents are for example protic-polar and aprotic solvents, which may be used alone or in an admixture of at least two solvents. Examples are: water, alcohols (methanol, ethanol, propanol, butanol), ethyleneglycolmonomethyl- or -monoethylether, ethers (dibutylether, tetrahydrofuran, dioxane, ethyleneglycol dimethylether, ethyleneglycoldiethylether, diethyleneglycoldiethylether, triethyleneglycoldimethylether), halogenated hydrocarbons (methylenchloride, chloroform, 1,2-dichloroethane, 1,1,1-trichlororethane, 1,1,2,2-tetrachloroethane), carboxylic esters and lactones (acetic acid ethylester, propionic acid methylester, benzoic acid ethylester, 2-methoxyethylacetate, γ-butyrolactone, δ-valerolactone, pivalolac tone), carboxylic acid amides and lactames; N,N-dimethylformamide, N,N-diethylformamide, N,N-dimethylacetamide, tetramethylurea, hexamethylphosphorous acidtriamide, γ-butyrolactame, ε-caprolactame, N-methylpyrrolidone, N-acetylpyrrolidone, N-methylcaprolactame; sulfoxides (dimethylsulfoxide), sulfones (dimethylsulfone, diethylsulfone, trimethylenesulfone, tetramethylenesulfone), tertiary amines (N-methylpiperidine, N-methylmorpholine), aliphatic and aromatic hydrocarbons like petroleumether, pentane, hexane, cyclohexane, methylcyclohexane, benzene or substituted benzenes (chlorobenzol, o-dichlorobenzene, 1,2,4-tri-chlorobenzene, nitrobenzene, toluene, xylene) and nitrites (acetonitrile, propionitrile, benzenenitrile, phenylacetonitrile), ketones (acetone, methyl-isobutyl-ketone).

The coprecipitation may be carried out in by a number of methods. When the host and guest chromophores possess solubilities affording the desired weight range in the final composition, the precipitation may be completed by adding the solution to a non-solvent, filtering off then the precipitate and removing the solvent, preferably in drying the solid at elevated temperatures and preferably under vacuum. Another possibility is to simply evaporate the solvent under vacuum and/or elevated temperatures.

In the process of freeze-drying, a steady state of components and solvent in general is generated by freezing a solution, wherein the components are in homogeneous distribution. This state is maintained upon removal of the solvent by freeze-drying. The furnished materials are usually highly fluorescent and exhibit all the features characteristic of host/guest materials.

In another preferred embodiment the host and guest chromophores are dissolved in a suitable solvent, and then this solution is added to a polymer gel (polymer swollen with a solvent). Usually the host and guest chromophores are in turn soaked into the gel. As a rule, removal of the solvent and drying generates a composition according to the invention.

In another preferred embodiment host and guest chromophores are milled together using a ball mill. Due to the high shearing forces usually the guest chromophore particles and/or molecules penetrate into the host chromophore matrix, forming a fluorescent composition according to the invention.

In another preferred embodiment the host and guest chromophores are mixed, optionally together with a polymer, and then melt-mixed at temperatures below the respective decomposition temperatures of the individual components.

The compositions on hand can span a broad number of applications. For example, the inventive compositions could be rendered very useful as coloring agents in applications such as road markings and traffic signs for night and daylight uses, as they exhibit brilliant daylight fluorescence and can also be excited by the UV radiation of motor vehicles halogen lamps, thereby providing intense, bright colors during both day and nighttime. Other applications include their use as pigments, coloring agents, materials for scintillators, materials for solar energy collectors, materials for light emitting electroluminescent devices, materials for generating fluorescent images. Moreover, the choice of guest compound can lend a lot of flexibility to the desired emission wavelength required of the overall system, therein imparting the capability for color-tuning and ease of tailoring of the core system to specific color applications via wavelength modulation. It is also possible to produce fluorescent images (high relief structures) by the well known photoresist technology. The compositions of the invention may also be used in paints, lacquers and printing inks.

The compositions according to the invention may be used in various forms depending upon the end use purpose.

The compositions according to the invention may be milled to generate a powdery form for industrial applications.

Another embodiment of the invention is a composition according to the invention in form of a powder, which contains particles. The particles may have an average diameter from 10 nm to 500 µm, more preferably 50 nm to 100 µm and most preferably 50 nm to 50 µm. The powders also include polymer particles containing the host and guest chromophores dissolved and uniformly distributed therein, and can be obtained via grinding or emulsion polymerization, or both.

The particles of the composition of the invention may be encapsulated with polymers by known methods to generate for example pigments for coloring polymers. The compositions according to the invention may be used as a coating to form a layer on support materials, preferably via a process of co-sublimation. A further embodiment of the invention is a support material to which on at least partially is coated a layer of the composition according to the invention.

Suitable support (or carrier) materials may be selected from the group consisting of organic or inorganic materials like glass, ceramics, minerals, plastics, paper, wood, semiconductors, metals, metal oxides and semiconductor metal oxides, and metal or semiconductor metalnitrides or -carbides.

The thickness of the layer depends on the desired use and usually may be from 0.01 to 1000 µm, preferably 0.05 to 500 µm, and especially preferred 0.1 to 100 µm.

The coatings may be protected by covering coatings which preferably are transparent. Such coatings are well known, in particular photocrosslinked coatings are useful for this purpose, and are well known in the art.

The powders according to the invention may be admixed with polymers. A further embodiment of the invention is a composition comprising (a) a polymer substrate, and (b) particles of the composition according to the invention, homogeneously distributed therein.

The amount of the particles may be for example 0.0001 to 90 weight %, preferably 0.1 to 90 weight % and more preferably 1 to 50 weight % of the total composition.

The polymer substrate may be selected from thermoplastics, polymer blends, thermosettings and structurally crosslinked polymers. The polymers may be homopolymers, copolymers, blockpolymers, graft polymers or random polymers.

The polymers may be opaque or translucent but preferably transparent. The polymers may be selected for example from the group of thermoplastic polymers like polyesters, polyamides, polyimides, polyamide-imides, polyamide esters, polyurethanes, polyureas, polyolefines; polymers from substituted olefines like vinylethers, vinylesters, vinylalcohols, vinylchloride, vinyldichloride, acetonitrile, acrylic acid, methacrylic acid, esters and amides of acrylic acid and methacrylic acid, styrene, chlorostyrene, methylstyrene, styrene sulfonic acid and their esters and amides, vinylcarbazole, vinylpyridine, vinylpyrrolidone: polymaleic acid and esters and amides therefrom; polyethers (for example from bisphenol-A diglycidyl ether), polysufones, polyketones, polyphenylsulfides, and polyacetales; and natural polymers and their derivatives like cellulose and its esters and ethers, and starch or derivatives of starch.

Examples of thermosetting resins and structurally crosslinked resins are polyepoxides, unsaturated polyesters, photocrosslinked resins for example from acrylic acid and/or methacrylic esters and/or amides from polyols and/or polyamines, melamine/formaldehyde resins, and phenol/formaldehyde resins; polymers from butadiene, isoprene and or chloroprene and copolymers with olefins, which may be crosslinked and of rubbery nature; as well as silicates obtainable for example through the known sol/gel process.

The thermoplastic compositions are for example obtainable by known mixing methods like admixing solutions of polymers and removing the solvent, injection molding and extrusion molding. Thermosetting and structurally crosslinked compositions are obtainable by known methods like press molding, whereby the particles usually are dispersed prior to the polymerization of a precursor composition.

The polymeric compositions of the invention may contain further ingredients to enhance certain features such as electrical, physical and mechanical properties, and/or the processability, for example dispersing agents to achieve a uniform distribution of particles, lubricants, plasticizers, antistatica, solvents, molding agents, antioxidants, light stabilizers, fillers and reinforcing fillers like glass balls and glass fibbers, silicates (e.g. mica, clay, wollastonite), metal and semiconductor metal oxides, metal carbonates, metal salts, metals and semiconductor metals, carbon black, as powder, or carbon fibers, whiskers, metal and semiconductor metal carbides, metal and semiconductor metal nitrides, dyes, pigments and others.

The polymer compositions of the invention me be used in the form of shaped articles.

The polymer composition or a polymerisable precursor composition with host/guest particles may contain a solvent to generate coating compositions. Suitable solvents are mentioned before.

In another aspect of the invention the polymer composition containing particles of the host/guest composition or particles from polymers and dissolved host/guest chromophores may be used as coatings on carrier materials, using the above mentioned composition.

Another embodiment of the invention is a composition comprising (a) a carrier material and (b) at least on one surface a coating of a composition comprising (a) a polymer substrate, and (b) particles of the composition, or particles from polymers and dissolved host/guest chromophores, or both according to the invention, homogeneously distributed therein.

In another aspect of the invention the composition containing a polymer and soluble host/guest chromophores may be used as coatings on carrier materials, using a solution of said composition.

Another embodiment of the invention is a composition comprising (a) a carrier material and (b) at least on one surface a coating of a composition comprising (a) a polymer matrix, and (b) a polymer and soluble host/guest chromophores according to the invention, homogeneously distributed therein.

Suitable carrier materials may be selected from organic or inorganic materials like glass, ceramics, minerals, plastics, paper, wood, textiles, semiconductors, metals, metal oxides and semiconductor metal oxides, and metal or semiconductor metal-nitrides or -carbides.

The thickness of the coating depends on the desired use and may be from 0.01 to 1000 µm, preferably 0.05 to 500 µm, and especially preferred 0.1 to 100 µm.

The coatings may be protected by covering coatings which preferably are transparent. Such coatings are well known, in particular photocrosslinked coatings are useful for this purpose, and are well known in the art.

The coated materials are obtainable by known methods like painting, casting or spincoating, directly or with dispersion of the polymeric compositions.

It is also possible to use a polymerisable composition containing polymer forming monomers or oligomeric precursors, in particular crosslinkable olefinically unsaturated monomers are useful in generating such coatings. The polymerization may be induced thermally or by actinic radiation or both. It is often preferred to carry-out the polymerisations in the presence of a radical initiator species. The coating compositions are novel and a further embodiment of the invention.

A further embodiment of the invention is a solvent containing liquid composition, comprising
(1) a soluble polymer, and
(2) particles of the host and guest chromophore of a composition according to the invention, or dissolved therein host and guest chromophores according to the invention.

These compositions may contain a solvent, such as those mentioned before, and optionally surfactants and dispersing agents. The viscosity range of the composition depends on the desired application, and can be readily by choice of solvent quantity, polymers binder and fluorescent materials. To further achieve a desired viscosity thickening agents may additionally be used. Suitable solvents have been mentioned.

The preparation of this composition can be achieved by simply mixing the ingredients together using suitable mixing equipment. Dispersions are in general stable depending upon the viscosity. Aggregated particles may be redistributed by stirring.

In a highly advantageous embodiment of preparing coatings polymerisable compositions can be used, wherein at least one surface of a carrier material is coated and subsequently polymerized by heat, radiation or both. Photopolymerizable mixtures can also be used to generate fluorescent images by known photoresist technology.

A further embodiment of the invention is a polymerisable composition comprising polymerisable monomers or prepolymers in admixture with a composition according to the invention in the form of a powder containing particles, or with host and guest chromophores according to the invention, preferably dissolved therein, or both.

The composition may be used to generate the polymers or polymer particles according to the invention as described before. Preferably the composition contains a solvent, when coatings or images are to be generated. The afore described embodiments also apply to this composition, inclusive of the preferred embodiments.

In a preferred embodiment the composition is based on polymerisable monomers and/or prepolymers containing a group selected from olefinically unsaturated groups, preferably from —CH=CH$_2$ and —C(CH$_3$)=CH$_2$, which can be thermally or photo-polymerized.

Photopolymerisable monomers and prepolymers are well known in the art and described for example in EP-A-0 654 711. Preferred photopolymerisable monomers and prepolymers are those based on the esters or amides of acrylic acid or methacrylic acid and alcohols, polyols, amines and polyamines.

Preferred ethylenically unsaturated photopolymerisable agents are selected from the group of acrylic or methacrylic acid esters of aliphatic, cycloaliphatic and cycloaliphatic-aliphatic alcohols and diols to tetrols, and amines and diamines to tetramines containing especially preferred 2 to 12, and particularly preferred 2 to 8 C-atoms. Some examples of these diols are alkylenediols like ethylenglycol, 1,2- or 1,3-propanediol, 1,2-, 1,3- and 1,4-butanediol, pentanediol, hexanediol, octanediol, decanediol, dodecanediol, cyclohexanediol, di(hydroxymethyl)-cyclohexane, polyoxyalkylendiols from preferably C$_2$–C$_6$alkylendiols with preferably 2 to 100 alkylenediol units, more preferably 2 to 50 alkylenediol units, and most preferably 2 to 20 alkylenediol units, like for example polyethylenediols, polypolypropylenediols, polybutylene-diols and polyethylene/polypropylenediols, further 1,1,1-trihydroxymethylethane or -propane, pentaerythritol and dipentaerythritol. Some examples for polyamines are ethylenediamine, 1,3- and 1,3-propanediamine, 1,2-, 1,3- and 1,4-butanediamine, 1,6-hexanediamine, diethylenetriamine, triethylenetetramine, cyclohexanediamine, (aminomethyl)cyclohexaneamine, isophorondiamine and di(aminomethyl)cyclohexane. Examples of alcohols are linear or branched C$_1$ to C$_{20}$alkanols.

The photopolymerisable composition may be particularly suitable for generating coatings and images.

A further embodiment of the invention is a composition comprising a carrier material with a high relief image of a polymerized photoresist material, which contains a composition according to the invention in the form of a powder containing particles, or host and guest chromophores according to the invention, or both, if desired dissolved and/or homogeneoulsly distributed therein.

A further embodiment of the invention is a process for the preparation of fluorescent high relief images on a carrier. Preferably, this involves irradiating under a mask or by laser writing, the above coated photopolymerisable composition (which preferably has been dried and removed of solvent) on the carrier, developing the irradiated composition and finally removing the non-irradiated parts.

Removal of the non-irradiated parts in general is mostly carried out by treatment with solvent.

All highly fluorescent materials described before can broadly be used in optical and electrooptical devices.

A further embodiment of the invention is a process for the creation of fluorescent radiation which requires the excitation either electrically or by UV or visible radiation, or both, of a fluorescent composition according to the invention.

Another embodiment of the invention is the use of the compositions according to the invention as fluorescent materials.

As described before benzo [4,5] imidazo [2,1-a] isoindol-11-one, 1,2,3,4-tetrachloro-benzo [4,5] imidazo [2,1-a] isoindol-11-one and some substituted derivatives are known in the art. From our investigations it was found that benzo [4,5] imidazo [2,1-a] isoindol-11-ones and 1,2,3,4-tetrachloro-benzo [4,5] imidazo [2,1-a] isoindol-11-ones show very high light stabilities, as measured by a time dependent exposure testing. Furthermore, it was found that the light stability of these compounds is reduced by substitution in the 7- and/or 8-positions. In the case of 1,2,3,4-tetraphenyl-benzo [4,5] imidazo [2,1-a] isoindol-11-one, it exhibits a moderate light stability, which suffices for a number of applications. However it was found, that the solid state luminescence is maintained, the light stability is greatly improved, and the compounds have a desired solubility, when the benzo [4,5] imidazo [2,1-a] isoindol-11-one is substituted in the 1-, 2-, 3- and/or 4-positions and in the 7- and/or 8-positions with selected substituents.

A further embodiment of the invention a compound of the formula V,

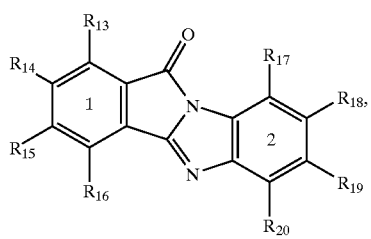

(V)

wherein
at most three of $R_{13}$, $R_{14}$, $R_{15}$ and $R_{16}$ are H and at least one of $R_{13}$, $R_{14}$, $R_{15}$ and $R_{16}$ are a substituent selected from the group of $C_1$ to $C_{18}$alkyl, $C_1$ to $C_{18}$alkoxy, $C_1$ to $C_{18}$alkylthio, $C_1$ to $C_{12}$alkoxy-poly$C_2$ to $C_6$oxyalkylene; unsubstituted or with F, Cl, Br, —CN, $C_1$ to $C_{12}$alkyl, $C_1$ to $C_{12}$alkoxy, $C_1$ to $C_{12}$alkylthio, or —NR$_{21}$R$_{22}$ substituted $C_5$ to $C_8$cycloalkyl, $C_5$ to $C_8$cycloalkoxy, $C_5$ to $C_8$cycloalkylthio, $C_5$ to $C_8$cycloalkyl-$C_1$ to $C_4$alkyl, $C_5$ to $C_8$cycloalkyl-$C_1$ to $C_4$alkoxy, $C_5$ to $C_8$cycloalkyl-$C_1$ to $C_4$alkylthio, phenyl, phenyloxy, phenylthio, phenyl-$C_1$ to $C_4$alkyl, phenyl-$C_1$ to $C_4$alkoxy, phenyl-$C_1$ to $C_4$alkylthio; or $R_{13}$ and $R_{14}$ together, $R_{15}$ and $R_{16}$ together, or $R_{13}$ and $R_{14}$ together and $R_{15}$ and $R_{16}$ together, or $R_{14}$ and $R_{15}$ together are selected from the groups —CH=CR$_{24}$—CR$_{25}$=CH—, —N=CR$_{24}$—CR$_{25}$=CH—, —CH=CR$_{24}$—CR$_{25}$=N—, —CH=N—CR$_{25}$=CH—, —CH=CR$_{24}$—N=CH—, —N=CR$_{24}$—CR$_{25}$=N—, —N=CR$_{24}$—N=CH—, —CH=CH—O—, —CH=CH—S—, —CH=CH—NR$_{23}$—;

$R_{17}$ and $R_{20}$ independently from one another are H or have the meaning of $R_{18}$; one of $R_{18}$ and $R_{19}$ are H and the other of $R_{18}$ and $R_{19}$ or both are a substituent selected from the group of $C_1$ to $C_{18}$alkyl, $C_1$ to $C_{18}$alkoxy, $C_1$ to $C_{18}$alkylthio, $C_1$ to $C_{12}$ alkoxy-poly$C_2$ to $C_6$ oxyalkylene; unsubstituted or with F, Cl, Br, —CN, $C_1$ to $C_{12}$alkyl, $C_1$ to $C_{12}$alkoxy, $C_1$ to $C_{12}$ alkylthio, or —NR$_{21}$R$_{22}$ substituted $C_5$ to $C_8$cycloalkyl, $C_5$ to $C_8$cycloalkoxy, $C_5$ to $C_8$ cycloalkylthio, $C_5$ to $C_8$cycloalkyl-$C_1$ to $C_4$alkyl, $C_5$ to $C_8$cycloalkyl-$C_1$ to $C_4$alkoxy, $C_5$ to $C_8$cycloalkyl-$C_1$ to $C_4$alkylthio, phenyl, phenyloxy; phenylthio, phenyl-$C_1$ to $C_4$alkyl, phenyl-$C_1$ to $C_4$alkoxy, phenyl-$C_1$ to $C_4$alkylthio, phenyl-$C_2$ to $C_{12}$alkylidene, phenyl-C(O)—, phenyl-NR$_{23}$—C(O)—, phenyl-NR$_{23}$—S(O)$_2$—, phenyl-S(O)—, phenyl-S(O)$_2$—, phenyl-CO$_2$—, phenyl-S(O)—O—, phenyl-SO$_3$—, phenyl-NR$_{23}$—, or phenyl-CH=CH—; or $R_{17}$ and $R_{18}$ together, $R_{19}$ and $R_{20}$ together, or $R_{17}$ and $R_{18}$ together and $R_{19}$ and $R_{20}$ together, or $R_{18}$ and $R_{19}$ together are selected from the groups —CH=CR$_{24}$—CR$_{25}$=CH—, —N=CR$_{24}$—CR$_{25}$=CH—, —CH=CR$_{24}$—CR$_{25}$=N—, —CH=N—CR$_{25}$=CH—, —CH=CR$_{24}$—N=CH—, —N=CR$_{24}$—CR$_{25}$=N—, —N=CR$_{24}$—N=CH—, —CH=CH—O—, —CH=CH—S—, —CH=CH—NR$_{23}$—;

$R_{21}$ and $R_{22}$ are independently from one another are $C_1$ to $C_{20}$alkyl, phenyl, $C_1$ to $C_{12}$ alkylphenyl, benzyl or $C_1$ to $C_{12}$alkylbenzyl, or $R_{21}$ and $R_{22}$ together mean tetramethylene, pentamethylene or —CH$_2$CH$_2$—O—CH$_2$CH$_2$—;

$R_{23}$ is H $C_1$ to $C_4$alkyl or benzyl; and $R_{24}$ and $R_{25}$ are independently from one another H, $C_1$ to $C_6$alkyl, $C_1$ to $C_6$alkoxy, $C_1$ to $C_6$alkylthio, or F, Cl or Br.

In a preferred embodiment $R_{13}$ and $R_{14}$ are substituents, and most preferably $R_{13}$, $R_{14}$, $R_{15}$ and $R_{16}$ are substituents. In still another preferred embodiment, $R_{13}$ and $R_{14}$, $R_{15}$ and $R_{16}$, $R_{14}$ and $R_{15}$, or $R_{13}$ and $R_{14}$ and $R_{15}$ and $R_{16}$ each together mean —CH=CR$_{24}$—CR$_{25}$=CH—, —N=CR$_{24}$—CR$_{25}$=CH—, —CH=CR$_{24}$—CR$_{25}$=N—, —CH=N—CR$_{25}$=CH—, —CH=CR$_{24}$—N=CH—.

In an other preferred embodiment $R_{17}$ and $R_{20}$ mean H, and $R_{17}$ and $R_{19}$ or both are substituents. In still another preferred embodiment, $R_{17}$ and $R_{18}$, $R_{19}$ and $R_{20}$, $R_{18}$ and $R_{19}$, or $R_{17}$ and $R_{18}$ and $R_{19}$ and $R_{20}$ each together mean —CH=CR$_{24}$—CR$_{25}$=CH—, —N=CR$_{24}$—CR$_{25}$=CH—, —CH=CR$_{24}$—CR$_{25}$=N—, —CH=N—CR$_{25}$=CH—, —CH=CR$_{24}$—N=CH—.

In the context of the invention when one or more of $R_{13}$, $R_{14}$, $R_{15}$ and $R_{16}$ as well as $R_{17}$, $R_{18}$, $R_{19}$ and $R_{20}$ is alkyl, it maybe linear alkyl or branched alkyl, and contain preferably 1 to 12 and more preferably 1 to 6 carbon atoms. Examples for alkyl have been given before. Preferred alkyls are methyl, ethyl, n- or i-propyl, n-, I- and t-butyl, and the isomers of pentyl and hexyl.

In the context of the invention when one or more of $R_{13}$, $R_{14}$, $R_{15}$ and $R_{16}$ as well as $R_{17}$, $R_{18}$, $R_{19}$ and $R_{20}$ is alkoxy, it maybe linear alkoxy or branched alkoxy, and contain preferably 1 to 12 and more preferably 1 to 6 carbon atoms. Examples for alkoxy have been given before. Preferred alkoxies are methoxy, ethoxy, n- or i-propoxy, n-, I- and t-buoxty, and the isomers of pentoxy and hexoxy.

In the context of the invention when one or more of $R_{13}$, $R_{14}$, $R_{15}$ and $R_{16}$ as well as $R_{17}$, $R_{18}$, $R_{19}$ and $R_{20}$ is alkylthiols, it maybe linear alkylthiol or branched alkylthiol, and contain preferably 1 to 12 and more preferably 1 to 6 carbon atoms. Examples for alkylthio have been given before. Preferred alkylthiols are methylthio, ethylthio, n- or i-propylthio, n-, I- and t-butylthio, and the isomers of pentylthio and hexylthio.

In the context of the invention when one or more of $R_{13}$, $R_{14}$, $R_{15}$ and $R_{16}$ as well as $R_{17}$, $R_{18}$, $R_{19}$ and $R_{20}$ is $C_1$ to $C_{12}$alkoxy-poly$C_2$ to $C_6$oxyalkylene, the alkoxy maybe linear alkoxy or branched alkoxy and contains preferably 1 to 6 and more preferably 1 to 4 carbon atoms and may be for example methoxy, ethoxy, propoxy and butoxy. The oxyalkylene group preferably contains 2 to 4 and more preferably 2 or 3 carbon atoms and may be ethylenoxy or 1,2-propylenoxy. The residue may contain 1 to 12, preferably 1 to 6, and more preferably 1 to 4 repeating oxyalkylene units.

In the context of the invention when one or more of $R_{13}$, $R_{14}$, $R_{15}$ is and $R_{16}$ as well as $R_{17}$, $R_{18}$, $R_{19}$ and $R_{20}$ is cycloalkyl, it is preferably cyclopentyl or cyclohexyl.

In the context of the invention when one or more of $R_{13}$, $R_{14}$, $R_{15}$ and $R_{16}$ as well as $R_{17}$, $R_{18}$, $R_{19}$ and $R_{20}$ is cycloalkoxy it is preferably cyclopentoxy or cyclohexoxy.

In the context of the invention when one or more of $R_{13}$, $R_{14}$, $R_{15}$ and $R_{16}$ as well as $R_{17}$, $R_{18}$, $R_{19}$ and $R_{20}$ is cycloalkyltho it is preferably cyclopentylthio or cyclohexylthio.

In the context of the invention when one or more of $R_{13}$, $R_{14}$, $R_{15}$ and $R_{16}$ as well as $R_{17}$, $R_{18}$, $R_{19}$ and $R_{20}$ is cycloalkyl-alkyl, the alkyl is preferably ethyl and most preferably methyl, and the cycloalkyl is preferably cyclopentyl or cyclohexyl. Preferred examples are cyclopentylmethyl and cyclohexylmethyl.

In the context of the invention when one or more of $R_{13}$, $R_{14}$, $R_{15}$ and $R_{16}$ as well as $R_{17}$, $R_{18}$, $R_{19}$ and is cycloalkyl-alkoxy, the alkoxy is preferably ethoxy and most preferably methoxy, and the cycloalkyl is preferably cyclopentyl or cyclohexyl. Preferred examples are cyclopentyl-methoxy and cyclohexylmethoxy.

In the context of the invention when one or more of $R_{13}$, $R_{14}$, $R_{15}$ and $R_{16}$ as well as $R_{17}$, $R_{18}$, $R_{19}$ is cycloalkyl-alkylthio, the alkylthio is preferably ethylthio and most preferably methylthio, and the cycloalkyl is preferably cyclopentyl or cyclohexyl. Preferred examples are cyclopentyl-methylthio and cyclohexylmethylthio.

In the context of the invention when one or more of $R_{13}$, $R_{14}$, $R_{15}$ and $R_{16}$ as well as $R_{17}$, $R_{18}$, $R_{19}$ and $R_{20}$ is phenylalkyl the alkyl group preferably contains 1 or 2 carbon atoms and mostly preferred is methyl. Especially preferred is benzyl.

In the context of the invention when one or more of $R_{13}$, $R_{14}$, $R_{15}$ and $R_{16}$ as well as $R_{17}$, $R_{18}$, $R_{19}$ and $R_{20}$ is phenylalkoxy, the alkoxy group preferably contains 1 or 2 carbon atoms and mostly preferred is methoxy. Especially preferred is benzyloxy.

In the context of the invention when one or more of $R_{13}$, $R_{14}$, $R_{15}$ and $R_{16}$ as well as $R_{17}$, $R_{18}$, $R_{19}$ and $R_{20}$ is phenylalkylthio, the alkylthio group preferably contains 1 or 2 carbon atoms and mostly preferred is methylthio. Especially preferred is benzylthio.

In the context of the invention when one or more of $R_{17}$, $R_{18}$, $R_{19}$ and $R_{20}$ is phenyl-$C_2$ to $C_{12}$alkylidene, the alkylidene may be linear or branched and may contain 2 to 6 and preferably 2 to 4 carbon atoms. Some examples are ethylidene, 1,1- or 2,2-propylidene, and 1,1- or 2,2-butylidene.

Preferred substituents are F, Cl, $C_1$ to $C_4$alkyl, $C_1$ to $C_4$alkoxy, $C_1$ to $C_4$alkylthio, and —$NR_{21}R_{22}$, wherein $R_{21}$ and $R_{22}$ are independently from one another is $C_1$ to $C_{12}$alkyl, phenyl or benzyl.

In the context of the invention when $R_{21}$ and $R_{22}$ are alkyl it may be linear alkyl or branched alkyl and may contain 1 to 12 and preferably 1 to 6 carbon atoms.

In the context of the invention when $R_{21}$ and $R_{22}$ are alkylphenyl, the alkyl may be linear or branched and may contain 1 to 8 and preferably 1 to 6 carbon atoms.

In the context of the invention when $R_{21}$ and $R_{22}$ are alkylbenzyl, the alkyl may be linear or branched and may contain 1 to 8 and preferably 1 to 6 carbon atoms.

$R_{23}$ is preferably H, methyl or ethyl.

In the context of the invention when $R_{24}$ and $R_{25}$ are alkyl, alkoxy, alkylthio may be linear or branched and may contain 1 to 4 and preferably 1 or 2 carbon atoms.

In a preferred embodiment $R_{13}$, $R_{14}$, $R_{15}$ and $R_{16}$ are preferably $C_1$ to $C_4$alkyl, $C_1$ to $C_4$alkoxy, phenyl, or $C_1$ to $C_4$alkylphenyl. Mostly preferred $R_{13}$, $R_{14}$, $R_{15}$ and $R_{16}$ are all phenyl.

In still a further preferred embodiment $R_{17}$ and $R_{20}$ are H, and $R_{18}$ and $R_{19}$ or both are $C_1$ to $C_{18}$alkyl or $C_1$ to $C_{18}$alkoxy, or $R_{17}$ and $R_{18}$, $R_{19}$ and $R_{20}$, $R_{18}$ and $R_{19}$, or $R_{17}$ and $R_{18}$ and $R_{19}$ and $R_{20}$ each together mean —CH=$CR_{24}$—$CR_{25}$=CH—, wherein $R_{24}$ and $R_{25}$ mean independently from one another H, F, Cl, $C_1$ to $C_8$alkyl or $C_1$ to $C_8$alkoxy.

In an especially preferred embodiment the compounds of formula V correspond to formula VI,

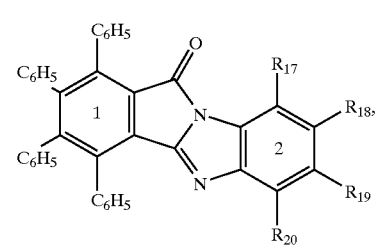

(VI)

wherein
$R_{17}$ and $R_{20}$ are H, and $R_{18}$ and $R_{19}$ or both are $C_1$ to $C_{18}$alkyl or $C_1$ to $C_{18}$ alkoxy, or $R_{18}$ and $R_{19}$ together mean —CH=$CR_{24}$—$CR_{25}$=CH—; or $R_{17}$ and $R_{18}$ together or $R_{19}$ and $R_{20}$ together, or $R_{17}$ and $R_{18}$ together and $R_{19}$ and $R_{20}$ together mean —CH=$CR_{24}$—$CR_{25}$=CH—, wherein $R_{24}$ and $R_{25}$ are independently from one another H, F, Cl, $C_1$ to $C_8$alkyl or $C_1$ to $C_8$alkoxy. The alkyl is preferably branched in the α- or α,α-position.

It was also found that 1,2,3,4-tetrachloro-benzo[4,5]imidazo[2,1-a]isoindol-11-ones with α-branched alkyl substituents possess a higher light stability than the methyl substituted compounds, and that acyl substituted 1,2,3,4-tetrachloro-benzo[4,35] imidazo[2,1-a] isoindol-11-ones have also a high light stability and a desired solubility. A further embodiment of the invention are compounds of the formula VIa,

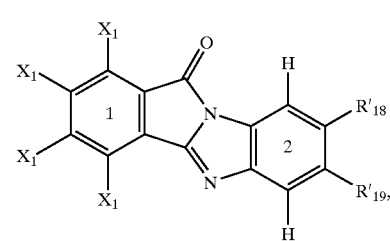

(VIa)

wherein
$X_1$ is Cl or Br,
one of $R'_{18}$ and $R'_{19}$ or both are independently from one another —COOH, or α- or α,α-branched $C_3$ to $C_{20}$alkyl or $R_a$—C(O)—, wherein $R_a$ means $C_1$ to $C_{20}$alkyl; or $C_5$ to $C_8$cycloalkyl, $C_5$ to $C_8$cycloalkyl-$CH_2$—, phenyl, benzyl, which are unsubstituted or substituted with halogen, $C_1$ to $C_{12}$alkyl or $C_1$ to $C_{12}$alkoxy, or
one of $R'_{18}$ and $R'_{19}$ is α- or α,α-branched $C_3$ to $C_{20}$alkyl or $R_a$—C(O)—, wherein $R_a$ means $C_1$ to $C_{20}$alkyl; or $C_5$ to $C_8$cycloalkyl, $C_5$ to $C_8$cycloalkyl-$CH_2$—, phenyl, benzyl, which are unsubstituted or substituted with halogen, $C_1$ to $C_{12}$alkyl or $C_1$ to $C_{12}$alkoxy, and the other of $R'_{18}$ and $R'_{19}$ is linear $C_1$ to $C_{12}$alkyl.

The branched alkyl is preferably selected from 1-methyl or 1,1-dimethyl substituted alk-1-yl. The alkyl preferably contains 3 to 18, more preferably 3 to 12, and most preferably 3 to 8 carbon atoms. $X_1$ is preferably Cl.

$R_a$ means preferably $C_3$ to $C_{12}$alkyl; or cyclopentyl, cyclohexyl, phenyl, benzyl, which are unsubstituted or substituted with F, Cl, Br, $C_1$ to $C_6$alkyl or $C_1$ to $C_6$alkoxy.

In the context of the invention the linear alkyl contains preferably 1 to 8, more preferably 1 to 6, and most preferably 1 to 4 carbon atoms.

Compounds of the formulae V, VI and VIa can be prepared in analogy to known methods, e.g. described in EP-A 456 609, wherein the preparation method is based on the following equation:

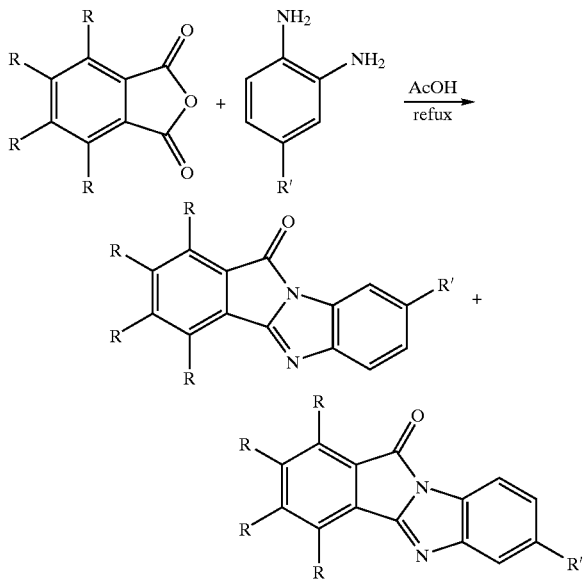

Usually the two isomers indicated above are obtained which can be separated, if desired, e.g. by column chromatography. In general, it is not necessary for the success of this invention to separate the two structural isomers.

Another preferred embodiment of the present invention relates to the use of the inventive compounds V, VI and VIa as organic emitting materials in and for the preparation of electroluminescence ("EL") devices. Those EL-devices are well known in the art and e.g. described in U.S. Pat. No. 5,593,788, WO 94/15441, and the literature cited therein. For example one of the common EL devices comprises two extremely thin layers (<1.0 μm in combined thickness) which separate the anode and the cathode. One layer specifically is chosen to inject and transport holes and the other specifically chosen to inject and transport electrons and also acting as the organic luminescent zone of the device. The extremely thin organic luminescent medium offers reduced resistance, permitting higher current densities for a given level of electrical biasing. Since light emission is directly related to current density through the organic luminescent medium, the thin layers coupled with increased charge injection and transport efficiencies have allowed acceptable light emission levels (e.g. brightness levels capable of being visually detected in ambient light) to be achieved with low voltages in ranges compatible with integrated circuit drivers, such as transporting layer also acting as the luminescent zone of the device.

In another preferred embodiment of this invention, the inventive host/guest compositions can be used as organic emitting material in a layer of an EL device as well as for the preparation of such an EL device. Such devices are known in principle e.g. from U.S. Pat. No. 5,593,788 and the prior art cited therein, hence, no further details are necessary for a skilled person in the art.

Hence, electroluminescent devices comprising the inventive compounds or compositions are also part of this invention. The preparation of such devices is given in detail e.g. in the above cited U.S. Pat. No. 5,593,788 or WO 94/15441.

The fluorescent composition of the present invention emits solid state fluorescence with a greatly enhanced emission intensity when compared to the solid-state emission intensity of a powder that contains host units but lacks any guest units, or a powder that contains guest units but lacks any host units.

The compositions on hand do show the following advantages compared to known compositions:

a) a greatly enhanced and intense fluorescence emission is generated, b) an intense solid state fluorescence is imparted, wherein the emission wavelengths are in the in the visible region of the electromagnetic spectrum, c) the composition can be excited using wavelengths in both the UV and visible regions, d) very good photostabilities and outdoor durabilities can be achieved, e) a wide range of emission wavelengths can be achieved through selection of guest mole cules (color tuning), f) a high thermal stability can be achieved, g) easy preparation for the materials i.e. co-precipitation of the dissolved components is possible.

The following examples demonstrate the invention.

The designation of the benzo [4,5] imidazo [2,1-a] isoindol-11-ones relies on the following formula:

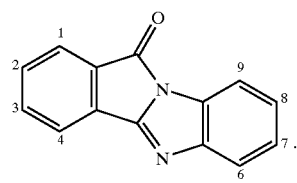

A) Preparation of benzo [4,5] imidazo [2,1-a] isoindol-11-ones

EXAMPLE A1

1,2,3,4-tetraphenyl-benzo [4,5] imidazo [2,1-a] isoindol-11-one-7(or 8, A'1)-carboxylic acid (A1)

A 300 ml round-bottom flask equipped with a stirrer and reflux condenser is charged with 4.58 g (30.1 mmol) of 3,4-diaminobenzoic acid, 13.6 g (30.0 mmol) of 1,2,3,4-tetraphenyl-phthalic anhydride, and 100 ml of glacial acetic acid. Under nitrogen atmosphere, the mixture is stirred and heated at reflux for 5 hours. The slurry is cooled and the yellow solid is isolated by filtration. The solid is washed with water and then with methanol. 10.9 g of yellow solid is obtained (64%).

$^1$H-NMR (CDCl$_3$, TMS): δ 8.43 (d, J=1.2 Hz, 1H, $H_{A9}$ or $H_{A'6}$), 8.33 (d, J=0.9 Hz, 1H, $H_{A9}$ or $H_{A'6}$), 8.05 (dd, J=1.5, 8.4 Hz, 1H, $H_{A7}$ or $H_{A'8}$), 7.96 (dd, J=1.6, 8.5 Hz, 1H, $H_{A7}$ or H$_{A'8}$), 7.72 (d, J=8.3 Hz, 1H, H$_{A6}$ or H$_{A'9}$), 7.61 (d, J=8.5 Hz, 1H, H$_{A6}$ or H$_{A'9}$), 7.30–7.24 (m, 8H), 7.18–7.15 (m, 2H), 6.92–6.89 (m, 6H) 6.81–6.76 (m, 4H).

EXAMPLE A2

1,2,3,4-tetraphenyl-7-(t-butyl)-benzo [4,5] imidazo [2,1-a] isoindol-11-one (A2) and 1,2,3,4-tetraphenyl-8-(t-butyl)-benzo [4,5] imidazo [2,1-a] isoindol-11-one (A'2)

A 100 ml round-bottom flask equipped with a stirrer and reflux condenser is charged with 0.99 g (6.01 mmol) of 4-(t-butyl)-o-phenylenediamine, 2.73 g (6.03 mmol) of 1,2,3,4-tetraphenyl-phthalic anhydride, and 15 ml of glacial acetic acid. Under nitrogen atmosphere, the mixture is stirred and heated at reflux for 3 hours. The slurry is cooled and the yellow solid is isolated by filtration. The solid is washed with water. 2.5 g of yellow solid is obtained (total 71%; 42% for A2 and 29% for A'2). Two isomers can be separated by column chromatography using CH$_2$Cl$_2$ as eluent.

A2 (7-position):
$^1$H-NMR (CDCl$_3$, TMS): δ 7.60 (d, J=1.3 Hz, 1H, H$_6$), 7.58 (d, J=8.4 Hz, 1H, H$_9$), 7.30 (dd, J=8.5, 1.4 Hz, 1H, H$_8$), 7.30–7.16 (m, 10H), 6.87–6.83 (m, 6H), 6.81–6.76 (m, 4H), 1.29 (s, 9H).
$^{13}$C-NMR (in CDCl$_3$): δ 160.3 (s, C=O), 156.1 (s, C$_{4b}$), 149.6 (dt, C$_{5a}$), 148.3 (m, C$_7$), 147.9 (t, C$_3$), 145.5 (t, C$_2$), 141.9 (t, C$_4$ or C$_1$), 138.4 (m), 138.1 (m), 137.7 (C$_4$ or C$_1$), 136.1 (m), 135.5 (m), 130.9, 130.8, 130.3, 130.1 (s), 129.8, 127.7, 127.5, 127.1, 127.0, 126.4, 126.3, 123.9 (dm, J$^1$=160 Hz, C$_8$), 118.7 (dd, J$^1$=160 Hz, C$_6$), 111.6 (d, J$^1$=170 Hz, C$_9$), 35.0 (CMe$_3$), 31.6 (CH$_3$).

A'2 (8-position):
$^1$H-NMR (CDCl$_3$, TMS): δ 7.73 (d, J=1.6 Hz, 1H, H$_9$), 7.47 (d, J=8.6 Hz, 1H, H$_6$), 7.28–7.22 (m, 9H), 7.20–7.17 (m, 2H), 6.93–6.89 (m, 6H), 6.82–6.78 (m, 4H), 1.32 (s, 9H).
$^{13}$C-NMR (CDCl$_3$): δ 160.6 (s, C=O), 155.6 (s, C$_2$), 150.3 (m, C$_8$), 147.9 (t, C$_3$), 147.4 (ddd, C$_{5a}$), 145.4 (t, C$_2$), 141.9 (t), 138.4 (m), 138.0 (m), 137.6 (t), 136.0 (m), 135.6 (m), 130.9, 130.8, 130.4, 130.2 (s), 129.8, 127.7, 127.5, 127.4, 127.1, 127.0, 126.3, 126.2, 122.4 (dd, J$^1$=160 Hz, C$_7$), 121.1 (d, J$^1$=160 Hz, C$_6$), 109.3 (ddd, J$^1$=160 Hz, C$_9$), 35.2 (CMe$_3$), 31.5 (CH$_3$).

EXAMPLE A3

1,2,3,4-tetraphenyl-benzo [4,5] imidazo [2,1-a] isoindol-11-one (A3)

A 500 ml round-bottom flask equipped with a stirrer and reflux condenser is charged with 8.34 9 (73.3 mmol) of o-phenylenediamine (95%), 33.0 g (66.3 mmol) of 1,2,3,4-tetraphenyl-phthalic anhydride, and 200 ml of glacial acetic acid. Under nitrogen atmosphere, the mixture is stirred and heated at reflux for 11 hours. The slurry is cooled and the yellow solid is isolated by filtration. The solid is washed with water and then with methanol. 35.1 g of an yellow solid is obtained (92%).
$^1$H-NMR (CDCl$_3$, TMS): δ 7.66 (d, J=7.6 Hz, 1H), 7.55 (d, J=7.7 Hz, 1H), 7.30–7.15 (m, 12H), 6.93–6.88 (m, 6H), 6.81–6.76 (m, 4H). MS: 524 ([M]$^+$).

EXAMPLE A4

1,2,3,4-tetraphenyl-7-(or 8)-nitro-benzo [4,5] imidazo [2,1-a] isoindol-11-one (A4, A'4)

A 100 ml round-bottom flask equipped with a stirrer and reflux condenser is charged with 1.53 g (9.99 mmol) of 4-nitro-o-phenylenediamine, 4.53 g (10.0 mmol) of 1,2,3,4-tetraphenyl-phthalic anhydride, and 25 ml of glacial acetic acid. Under nitrogen atmosphere, the mixture is stirred and heated at reflux for 1.33 hours. The slurry is cooled and the yellow solid is isolated by filtration. The solid is washed with water and then with methanol. 6.1 g of a pale yellow solid is obtained (100%).
$^1$H-NMR (CDCl$_3$, TMS): δ 8.57 (d, J=2.2 Hz, 1H, H$_{A9}$ or H$_{A'6}$), 8.48 (d, J=2.1 Hz, 1H, H$_{A9}$ or H$_{A'6}$), 8.22 (dd, J=2.1, 8.8 Hz, 1H, H$_{A7}$ or H$_{A'8}$), 8.13 (dd, 1H, H$_{A7}$ or H$_{A'8}$), 7.75 (d, J=8.8 Hz, 1H, H$_{A6}$ or H$_{A'9}$), 7.65 (d, J=8.9 Hz, 1H, H$_{A6}$ or H$_{A'9}$), 7.32–7.23 (m, 8H), 7.18–7.15 (m, 2H), 6.95–6.90 (m, 6H), 6.81–6.76 (m, 4H).
MS: 569 ([M]$^+$).

EXAMPLE A5

1,2,3,4-tetraphenyl-7(or 8)-methyl-benzo [4,5] imidazo [2,1-a] isoindol-11-one (A5, A'5)

A 100 ml round-bottom flask equipped with a stirrer and reflux condenser is charged with 1.30 g (10.64 mmol) of 4-methyl-o-phenylenediamine, 4.53 g (10.01 mmol) of 1,2,3,4-tetraphenyl-phthalic anhydride, and 25 ml of glacial acetic acid. Under nitrogen atmosphere, the mixture is stirred and heated at reflux for 5 hours. The slurry is cooled and the yellow solid is isolated by filtration. The solid is washed with water and MeOH. 4.16 g of a yellow solid is obtained (77%).
$^1$H-NMR (CDCl$_3$, TMS): δ 7.52 (d, J=8.1 Hz, 1H, H$_{A6}$ or H$_{A'9}$), 7.48 (br s, 1H, H$_{A9}$ or H$_{A'6}$), 7.42 (d, J=8.2 Hz, 1H, H$_{A6}$ or H$_{A'9}$), 7.36 (br s, 1H, H$_{A9}$ or H$_{A'6}$), 7.27–7.23 (m, 8H), 7.18–7.15 (m, 2H), 7.06 (br d, 1H, H$_{A7}$ or H$_{A'8}$), 6.99 (br d, 1H, H$_{A7}$ or H$_{A'8}$), 6.92–6.88 (m, 6H), 6.80 –6.75 (m, 4H).
MS: 538 ([M]$^+$), 537 ([M–H]$^+$).

EXAMPLE A6

1,2,3,4-tetraphenyl-7(or 8)-methoxy-benzo [4,5] imidazo [2,1-a] isoindol-11-one (A6, A'5).

A 100 ml round-bottom flask equipped with a stirrer and reflux condenser is charged with 1.38 g (9.99 mmol) of 4-methoxy-o-phenylenediamine, 4.52 g (9.99 mmol) of 1,2,3,4-tetraphenyl-phthalic anhydride, and 20 ml of glacial acetic acid. Under nitrogen atmosphere, the mixture is stirred and heated at reflux for 7 hours. The slurry is cooled and the yellow solid is isolated by filtration. The solid is washed with water, followed by purification with column chromatography. 3.75 g of yellow solid is obtained (68%).
$^1$H-NMR (CDCl$_3$, TMS): δ 7.52 (d, J=8.6 Hz, 1H, H$_{A6}$ or H$_{A'9}$), 7.42 (d, J=8.9 Hz, 1H, H$_{A6}$ or H$_{A'9}$), 7.27–7.23 (m, 8H), 7.20 (d, J=2.6 Hz, 1H, H$_{A9}$ or H$_{A'6}$), 7.19 –7.14 (m, 2H), 7.08 (d, J=2.4 Hz, 1H, H$_{A9}$ or H$_{A'6}$), 6.92–6.88 (m, 6H), 6.85 (dd, 1H, J=2.4, 8.7 Hz, H$_{A7}$ or H$_{A'8}$), 6.80–6.74 (m, 1H, H$_{A7}$ or H$_{A'8}$+4H).
MS: 554 ([M]$^+$).

EXAMPLE A7

1,2,3,4-tetraphenyl-6,7-8,9-dibenzo-benzo [4,5] imidazo [2,1-a] isoindol-11-one (A7)

A 100 ml round-bottom flask equipped with a stirrer and reflux condenser is charged with 0.84 g (4.03 mmol) of 9,10-diaminophenanthrene, 1.83 g (4.04 mmol) of 1,2,3,4-tetraphenyl-phthalic anhydride, and 15 ml of glacial acetic acid. Under nitrogen atmosphere, the mixture is stirred and heated at reflux for 5 hours. The slurry is cooled and the orange solid is isolated by filtration. The solid is washed with water and MeOH, followed by purification with column chromatography. 2.01 g of an orange solid is obtained (80%).

$^1$H-NMR (CDCl$_3$, TMS): δ 9.19 (dd, J=1.5, 8.0 Hz, 1H, H$_9$ or H$_{10}$), 8.70 (dd, J=7.8 Hz, 1H, H$_9$ or H$_{10}$), 8.64 (m, 1H, H$_6$ or H$_{13}$), 8.32 (m, 1H, H$_6$ or H$_{13}$), 7.64–7.59 (m, 4H, H$_{7,8,11,12}$), 7.37–7.28 (m, 8H), 7.25–7.22 (m, 2H), 6.96–6.90 (m, 6H), 6.86–6.79 (m, 4H).

EXAMPLE A8

1,2,3,4-tetrachloro-7(or 8)-nitro-benzo [4,5] imidazo [2,1-a] isoindol-11-one (A8, A'8)

A 200 ml round-bottom flask equipped with a stirrer and reflux condenser is charged with 2.30 g (15.0 mmol) of 4-nitro-o-phenylenediamine, 4.29 g (15.0 mmol) of 1,2,3,4-tetrachloro-phthalic anhydride, and 60 ml of glacial acetic acid. Under nitrogen atmosphere, the mixture is stirred and heated at reflux for 2 hours. The slurry is cooled and the pale yellow solid is isolated by filtration. The solid is washed with water and MeOH. 5.48 g of a pale yellow solid is obtained (91%).

$^1$H-NMR (CDCl$_3$, TMS): δ 8.75 (dd, J=1.7 Hz, 1H, H$_{A9}$ or H$_{A'6}$), 8.74 (dd, J=2.3 Hz, 1H, H$_{A9}$ or H$_{A'6}$), 8.40 (dd, J=2.2, 8.8 Hz, 1H, H$_{A7}$ or H$_{A'8}$), 8.32 (dd, J=2.3, 8.9 Hz, 1H, H$_{A7}$ or H$_{A'8}$), 7.97 (dd, J=8.7 Hz, 1H, H$_{A6}$ or H$_{A'9}$), 7.96 (dd, J=9.0 Hz, 1H, H$_{A6}$ or H$_{A'9}$).

MS: 403 ([M+2]$^+$), 401 ([M]$^+$).

EXAMPLE A9

1,2,3,4-tetrachloro-benzo [4,5] imidazo [2,1-a] isoindol-11-one-7(or 8)-carboxylic Acid (A9, A'9)

A 1 l round-bottom flask equipped with a stirrer and reflux condenser is charged with 15.2 g (100 mmol) of 3,4-diaminobenzoic acid, 28.6 g (100 mmol) of tetrachloro-phthalic anhydride, and 450 ml of glacial acetic acid. Under nitrogen atmosphere, the mixture is stirred and heated at reflux for 15 hours. The slurry is cooled and the greenish yellow solid is isolated by filtration. The solid is washed with water and methanol. 37.0 g of a greenish yellow solid is obtained (92%).

MS: 404 ([M+4]+), 402 ([M+2]+), 400 ([M]+), 387 ([M+4-OH]+), 385 ([M+2-OH]+), 383 ([M-OH]+).

EXAMPLE A10

1,2,3,4-tetrachloro-7(or 8)-(t-butyl)-benzo [4,5] imidazo [2,1-a] isoindol-11-one (A10, A'10)

A 100 ml round-bottom flask equipped with a stirrer and reflux condenser is charged with 2.48 g (15.1 mmol) of 4-(2'-methyl-2'-propyl)-o-phenylenediamine, 4.30 g (15.0 mmol) of tetrachloro-phthalic anhydride, and 40 ml of glacial acetic acid. Under nitrogen atmosphere, the mixture is stirred and heated at reflux for 3.5 hours. The slurry is cooled and the yellow solid is isolated by filtration. The solid is washed with water and methanol. 5.22 g of a yellow solid is obtained (84%).

$^1$H-NMR (CDCl$_3$, TMS): δ 7.82 (dd, J=0.5, 1.8 Hz, 1H, H$_{A9}$ or H$_{A'6}$), 7.73 (dd, J=0.5, 8.6 Hz, 1H, H$_{A6}$ or H$_{A'9}$), 7.42 (dd, J=1.8, 8.6 Hz, 1H, H$_{A7}$ or H$_{A'8}$), 1.40 (s, 9H).

MS: 416 ([M+4]+), 414 ([M+2]+), 412 ([M]+), 401 ([M+4-CH3]+), 399 ([M+2-CH3]+), 397 ([M-cu3]+).

EXAMPLE A11

1,2,3,4-tetrachloro-7(or 8)-benzoyl-benzo [4,5] imidazo [2,1-a] isoindol-11-one (A11, A'11)

A 100 ml round-bottom flask equipped with a stirrer and reflux condenser is charged with 2.13 g (10.0 mmol) of 3,4-diaminobenzophenone, 2.87 g (10.0 mmol) of tetrachloro-phthalic anhydride, and 23 ml of glacial acetic acid. Under nitrogen atmosphere, the mixture is stirred and heated at reflux for 3.5 hours. The slurry is cooled and the yellow solid is isolated by filtration. The solid is washed with water and methanol, followed by dissolving in hot CHCl$_3$ with a soxhlet extractor to remove insoluble impurities. After condensation, 3.36 g of a yellow solid is obtained (72%).

$^1$H-NMR (CDCl$_3$, TMS): δ 8.28 (dd, 1H, H$_{A9}$ or H$_{A'6}$), 7.93 (dd, J=0.7, 8.5 Hz, 1H, H$_{A6}$ or H$_{A'9}$), 7.87–7.82 (m, 3H, H$_{A7}$ or H$_{A'8}$, and H2', 6'), 7.64 (tt. J=1.2, 7.5 Hz, 1H, H$_{3',5'}$) 7.52 (t, J=7.6 Hz. 2H, H$_{4'}$).

MS: 464 ([M+4]$^+$), 462 ([M+2]$^+$), 460 ([M]$^+$), 387 ([M+4-C$_6$H$_5$]$^+$), 385 ([M+2-C$_6$H$_5$]$^+$), 383 ([M-C$_6$H$_5$]$^+$), 359 ([M+4-C$_6$H$_5$CO]$^+$), 357 ([M+2-C$_6$H$_5$ CO]$^+$), 355 ([M-C$_6$H$_5$CO]$^+$).

EXAMPLE A12

1,2,3,4-tetrachloro-benzo [4,5] imidazo [2,1-a] isoindol-11-one (A12)

Compound A12 is prepared according to the procedure described in EP-A-0 456 609.

B) Preparation of Guest Chromophores

EXAMPLE B1

N,N'-dibenzyl-quinacridone (B1)

A 500 ml round-bottom flask equipped with a stirrer and reflux condenser is charged with 3.13 g (10.0 mmol) of quinacridone (hereinafter referred to QA), 17.11 g (100 mmol) of benzyl bromide, 138.21 g (1.00 mol) of K$_2$CO$_3$ and 200 ml of dimethylformamide (DMF). Under a nitrogen atmosphere, the mixture is stirred and heated at reflux for 7.5 hours. The slurry is cooled and the orange solid is isolated by filtration. The solid is washed with water acetone and ethanol. There yields 4.34 g of an orange solid (88%).

$^1$H-NMR (DMSO-d$_6$, Dimethylsulfoxide(DMSO)): δ 8.56 (s, 2H, H$_1$), 8.35 (dd, J=7.9 Hz, 2H, H$_5$), 7.79 (dt, J=8.2 Hz, 2H, H$_4$), 7.67(d, J=8.6 Hz, 2H, H$_2$), 7.37 (t, 4H, H$_3$), 7.33 (t, 2H, H$_6$), 7.31 (t, 2H, H$_7$), 7.27 (d, 4H, H$_8$), 5.29 (s, 4H, H$_9$).

EXAMPLE B2

N,N'-dibenzyl-diphenyl-diketopyrrolopyrrol

A 100 ml round-bottom flask equipped with a stirrer and reflux condenser is charged with 1.47 g (5.1 mmol) of diphenyl-diketopyrrolopyrrole (hereinafter referred to DPP), 3.44 g (20.1 mmol) of benzyl bromide, 1.38 g (10.0 mmol) of K$_2$CO$_3$ and 50 ml of DMF. Under nitrogen atmosphere, the mixture is stirred and heated at 100° C. for 42.5 hours. The slurry is cooled and the orange solid is isolated by filtration. The solid is washed with water and MeOH, followed by dissolving in hot CHCl$_3$. This CHCl$_3$ solution is applied to silica gel column using CH$_2$Cl$_2$ as eluent. After condensation, 1.21 g of an orange solid is obtained (51%).

$^1$H-NMR (CDCl$_3$, TMS): δ 7.75 (d, J=7.1 Hz, 4H, H$_1$), 7.49–7.43 (m, 6H, H$_2$ and H$_3$), 7.30 (t, J=7.4 Hz 4H H$_5$) 7.24 (t, J=7.3 Hz, 2H, H$_6$), 7.19 (d, J=7.4 Hz, 4H, H$_4$), 4.99 (s, 4H, H$_7$).

MS: 468 ([M]+).

C) Preparation of Fluorescent Compositions

EXAMPLE C1

1.0×10$^{-4}$ mol (0.0557 g) of A1 as a host compound and various amounts of Rhodamine 19 (Kodak Laboratory Chemicals) as a guest compound (B3) or Rhodamine 6G (Kodak Laboratory Chemicals) as a guest compound (B4) are dissolved in 20 ml of 1,2-dichloroethane and mixed. The solvent is then evaporated using a rotary evaporator (RE47, Yamato Scientific Co., LTD.) to obtain fluorescent powders including A1 and B3 or B4 of various concentrations.

Photoluminescence spectra of the fluorescent powders are measured using a fluorescence spectrophotometer in standard reflection mode (F-4500, HITACHI Co., LTD.) with a solid sample holder by exciting the host compound at absorption band thereof with monochromic light ($\lambda_{max}$=360 nm). The results are listed in Table 1.

TABLE 1

Fluorescent properties of fluorescent powders

| Host | Guest | Guest concentration (mol %) | Photoluminescence spectrum Peak wavelength (nm) | Peak intensity |
|---|---|---|---|---|
| A1 | none | 0 | 512 | 545 |
| A1 | B3 | 0.1 | 571 | 987 |
| A1 | B3 | 0.2 | 573 | 1040 |
| A1 | B3 | 0.5 | 580 | 869 |
| A1 | B4 | 0.2 | 579 | 968 |

EXAMPLE C2

1.0×10$^{-4}$ mol (0.0557 g) of A1 and various amounts of B1 are dissolved in 20 ml of 1,2-dichloroethane and mixed. The solvent is then sublimed by freeze-drying with a freeze-dryer (FD81. Tokyo Rikakikai Co., LTD.) to obtain fluorescent powders including A1 and B1 of various concentrations. Photoluminescence spectra of the fluorescent powders are measured in the same manner as in Example C1. The results are listed in Table 2.

TABLE 2

Fluorescent properties of fluorescent powders including A1 and B1

| Host | Guest | Guest concentration (mol %) | Photoluminescence spectrum Peak wavelength (nm) | Peak intensity |
|---|---|---|---|---|
| A1 | none | 0 | 510 | 570 |
| A1 | B1 | 0.1 | 563 | 687 |
| A1 | B1 | 0.2 | 565 | 1014 |
| A1 | B1 | 0.5 | 564 | 964 |

EXAMPLE C3

3.0×10$^{-4}$ mol (0.1706 g) of A2 or A'2 as a host compound and various amounts of B1 or B2 as a guest compound are dissolved in 20 ml of 1-methyl-2-pyrrolidone and mixed. The solution is then poured into 400 ml of water which is vigorously stirred with a homogenizer (ULTRA-TURRAX T25. IKA-Labortechnik). A precipitate is filtered and dried in vacuo at 60° C. to obtain fluorescent powders including A2 or A3 and B1 or B2 of various concentrations. Photoluminescence spectra of the fluorescent powders are measured in the same manner as in Example C1. The results are listed in Tables 3 and 4.

TABLE 3

Fluorescent properties of fluorescent powders including A2 and B1 or B2

| Host | Guest | Guest concentration (mol %) | Photoluminescence spectrum Peak wavelength (nm) | Peak intensity |
|---|---|---|---|---|
| A2 | none | 0 | 526 | 197 |
| A2 | B1 | 0.2 | 523 | 1155 |
| A2 | B1 | 0.5 | 524 | 2005 |
| A2 | B1 | 1.0 | 526 | 2555 |
| A2 | B1 | 2.0 | 528 | 2876 |
| A2 | B1 | 5.0 | 529 | 1579 |
| A2 | B2 | 1.0 | 534 | 2054 |
| A2 | B2 | 2.0 | 537 | 2324 |
| A2 | B2 | 5.0 | 542 | 2160 |

TABLE 4

Fluorescent properties of fluorescent powders including A'2 and B1 of

| Host | Guest | Guest concentration (mol %) | Photoluminescence spectrum Peak wavelength (nm) | Peak intensity |
|---|---|---|---|---|
| A'2 | none | 0 | 522 | 552 |
| A'2 | B1 | 1.0 | 524 | 2854 |
| A'2 | B1 | 2.0 | 525 | 3942 |
| A'2 | B1 | 5.0 | 529 | 2227 |

EXAMPLE C4

Carefully measured amounts of A1 as a host compound, B1 as a guest compound and an acrylic polymer (PMMA; polymethylmethacrylate, Aldrich Chemical Co. Inc.) are dissolved in CHCl$_3$/methanol (95/5 vol. %) (Wako Chemical Co. Ltd.), to yield a clear, homogeneous solution (5 wt % concentration). The mixture is then cast onto a glass substrate using a wire bar (KCC rod No. 8, RK Print-Coat Instruments) and the solvent removed. At this point the polymer film has the visual color and spectroscopic features typical of the precursor. Photoluminescence spectra of the fluorescent films are measured in the same manner as in Example C1. The results are listed in Table 5.

TABLE 5

Fluorescent properties of the polymer films

| A1 (wt %) | B1 (wt %) | PMMA (wt %) | Photoluminescence spectrum Peak wavelength (nm) | Peak intensity |
|---|---|---|---|---|
| 5 | 0 | 95 | 501 | 401 |
| 5 | 0.05 | 95 | 545 | 561 |
| 5 | 0.1 | 95 | 548 | 564 |
| 5 | 0.2 | 95 | 552 | 586 |
| 5 | 0.3 | 95 | 555 | 788 |
| 10 | 0 | 90 | 501 | 440 |
| 10 | 0.05 | 90 | 546 | 593 |
| 10 | 0.1 | 90 | 551 | 819 |

TABLE 5-continued

Fluorescent properties of the polymer films

| A1 (wt %) | B1 (wt %) | PMMA (wt %) | Photoluminescence spectrum | |
|---|---|---|---|---|
| | | | Peak wavelength (nm) | Peak intensity |
| 10 | 0.2 | 90 | 553 | 811 |
| 10 | 0.3 | 90 | 559 | 896 |
| 30 | 0 | 70 | 501 | 461 |
| 30 | 0.05 | 70 | 551 | 621 |
| 30 | 0.1 | 70 | 552 | 781 |
| 30 | 0.2 | 70 | 556 | 734 |
| 30 | 0.3 | 70 | 558 | 799 |

EXAMPLE C5

0.1 g of the fluorescent powder of Example C3, which includes A2 as host and B2 as guest, is dispersed in 1.0 g of a functional acrylate monomer [KAYARAD D310 (Nippon Kayaku Co.)] using a homogenizer (ULTRA-TURRAX T25. IKA-Labortechnik). 5.0 g of a 10 wt % of polyvinylalcohol (PVA-117, Kurare) aqueous solution is added over the period of about 10 minutes to the vigorously stirred dispersion to give an uniform suspension, and recrystallized $K_2S_2O_8$ as initiator is added at room temperature. The reaction mixture is removed of oxygen by bubbling with $N_2$ gas for approximately 30 minutes, then placed in a temperature controlled water bath at 80° C. for 10 hours. Highly cross-linked polymer particles containing fluorescent powder are obtained and isolated by filtration. The particles are then washed oftentimes with water and methanol. Drying is performed in a vacuum oven at 60° C. overnight. Yield 34.4%. Photoluminescence spectra of the fluorescent polymer particles are measured in the same manner as described in Example C1. The results are listed in Table 6.

TABLE 6

Fluorescent properties of fluorescent polymer powders.

| Host | Guest | Guest concentration (mol %) | Photoluminescence spectrum | |
|---|---|---|---|---|
| | | | Peak wavelength (nm) | Peak intensity |
| A2 | none | 0 | 525 | 370 |
| A2 | B2 | 5.0 | 538 | 1520 |

EXAMPLE C6

0.1 g of A2 as host, none or 0.002 g of B2 as guest and 1.0 g of a functional acrylate monomer (KAYARAD D310) are dissolved in 10 ml of 1-methyl-2-pyrrolidone. The solution is then poured dropwise into 200 ml of 2 wt % of polyvinyalcohol (PVA-117, Kurare) aqueous solution which is vigorously stirred with a homogenizer. A yellow precipitate with green fluorescence is immediately generated, to which the recrystallized initiator $K_2S_2O_8$ is added. The reaction mixture is removed of oxygen by bubbling through $N_2$ gas for approximately 30 minutes, and placed in a temperature controlled water bath at 80° C. for 10 hours. Highly crosslinked polymer particles are obtained and isolated by filtration. The particles are then washed oftentimes with water and methanol. Drying is performed in a vacuum oven at 60° C. overnight. Yield 42.5%. Photoluminescence spectra of the fluorescent polymer particles are measured in the same manner as described in Example C1. The results are listed in Table 7.

TABLE 7

Fluorescent properties of fluorescent polymer powders.

| Host | Guest | Guest concentration (mol %) | Photoluminescence spectrum | |
|---|---|---|---|---|
| | | | Peak wavelength (nm) | Peak intensity |
| A2 | none | 0 | 524 | 410 |
| A2 | B2 | 2.0 | 531 | 1790 |

EXAMPLE C7

To an all glass reaction flask fitted with a rubber seal, magnetic stirrer, and maintained under a nitrogen atmosphere, 30 ml of degassed water is charged and heated to 60° C. Maintaining the reaction temperature of 60° C., a degassed slurry of 2.08 g (20 wt %) A12, 5.12 g (49 wt %) ethylene glycol dimethacrylate, 3.1 g (30 wt %) methyl methacrylate, none or 0.103 g (1 wt %) Lumogen F Orange (BASF), 0.16 g 2,2'-Azobis(isobutyronitrile) and 10 ml chloroform are added in a single addition. The vigorously stirred reaction is allowed to proceed for 6 hours, and then the reaction mixture is filtered. The precipitate consists of bright orange particles, that are non-uniform in shape and size. These particles are washed with water several times and dried at the water aspirator. Final drying is performed in a vacuum oven at 60° C. overnight. Yield 90%. The polymer powder thus obtained is ground into a fine powder, via a standard laboratory mortar and pestle. Photoluminescence spectra of the fluorescent polymer powders are measured in the same manner as described in Example C1. The results are listed in Table 8.

TABLE 8

Fluorescent properties of fluorescent polymer powders.

| Host | Guest | Guest concentration (mol %) | Photoluminescence spectrum | |
|---|---|---|---|---|
| | | | Peak wavelength (nm) | Peak intensity |
| A12 | none | 0 | 511 | 242 |
| A12 | Lumogen F Orange | 1.0 | 584 | 680 |

EXAMPLE C8

Light Stability of 1,2,3,4-tetraphenyl-benzo [4,5] imidazo [2,1-a] isoindol-11-ones 1,2,3,4-tetraphenyl-7(or 8)-methoxy-benzo [4,5] imidazo [2,1-a] isoindol-11-one and various derivatives are charged in the sample holder used in Example C1. The samples are exposed to light with a Xenon lamp weather-ometer (WEL-15X-HC-B.Ec, Suga Test Instruments Co.) for 100 hours under the following conditions:

| | |
|---|---|
| light intensity: | 0.35 W/cm² at 340 nm, |
| temperature: | 63° C. at black panel, |
| humidity: | 50%. |

The intensity of the photoluminescence is measured prior to light exposure and the intensity loss in percent is measured after 100 hours of light exposure as described in example C1, comparing the peak heights. The results are summarized in table 9.

TABLE 9

Light stability of stability of 1,2,3,4-tetraphenyl-benzo [4,5] imidazo [2,1-a] isoindol-11-ones.

| Compound | $\lambda_{max}$ (nm) | Intensity prior to exposure | Intensity after exposure | Loss (%) |
|---|---|---|---|---|
| A3 | 505 | 1211 | 759 | 37 |
| A2 | 517 | 810 | 751 | 7 |
| A'2 | 505 | 2033 | 1595 | 22 |
| A5 | 533 | 488 | 390 | 20 |
| A6 | 556 | 45 | 45 | <1 |
| A7 | 598 | 159 | 152 | 4 |

EXAMPLE C9

Light Stability of 1,2,3,4-tetrachloro-7-methyl-benzo [4,5] imidazo [2,1-a] isoindol-11-one and Other Derivatives The procedure of example C8 is repeated but this time using 1,2,3,4-tetrachloro-7-methyl-benzo [4,5] imidazo [2,1-a] isoindol-11-one (A") as comparison with 1,2,3,4-tetrachloro-7-t-butyl-benzo [4,5] imidazo [2,1-a] isoindol-11-one (A10) and 1,2,3,4-tetrachloro-7-benzoyl-benzo [4,5] imidazo [2,1-a] isoindol-11-one (A11). The results are summarized in table 10.

TABLE 10

| Compound | $\lambda_{max}$(nm) | Intensity prior to exposure | Intensity after exposure | Loss (%) |
|---|---|---|---|---|
| A" | 534 | 170 | 142 | 17 |
| A10 | 546 | 156 | 136 | 11 |
| A11 | 524 | 273 | 247 | 10 |

What is claimed is:

1. A compound of the formula V,

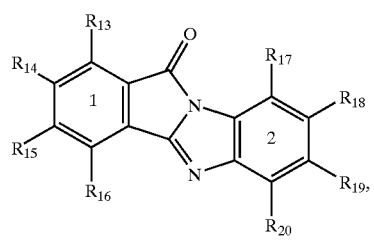

(V)

wherein $R_{13}$, $R_{14}$, $R_{15}$ and $R_{16}$ are a substituent selected from the group of $C_1$ to $C_4$alkyl, $C_1$ to $C_4$alkoxy, phenyl-$C_1$ to $C_4$alkyl, and phenyl;

$R_{17}$ and $R_{20}$ independently from one another are H, or have the meaning of $R_{18}$, one of $R_{18}$ and $R_{19}$ are H and the other of $R_{18}$ and $R_{19}$ or both are a substituent selected from the group of $C_1$ to $C_{18}$alkyl, $C_1$ to $C_{18}$alkoxy, $C_1$ to $C_{18}$alkylthio, $C_1$ to $C_{12}$alkoxy-poly$C_2$ to $C_6$-oxyalkylene; unsubstituted or with F, Cl, Br, —CN, $C_1$ to $C_{12}$alkyl, $C_1$ to $C_{12}$alkoxy, $C_1$ to $C_{12}$alkylthio, or —NR$_{21}$R$_{22}$ substituted $C_5$ to $C_8$cycloalkyl, $C_5$ to $C_8$cycloalkoxy, $C_5$ to $C_8$cycloalkylthio, $C_5$ to $C_8$cycloalkyl-$C_1$ to $C_4$alkyl, $C_5$ to $C_8$cycloalkyl-$C_1$ to $C_4$alkoxy, $C_5$ to $C_8$cycloalkyl-$C_1$ to $C_4$alkylthio, phenyl, phenyloxy, phenylthio, phenyl-$C_1$ to $C_4$alkyl, phenyl-$C_1$ to $C_4$alkoxy, phenyl-$C_1$ to $C_4$alkylthio, phenyl-$C_2$ to $C_{12}$alkylidene, phenyl-C(O)—, phenyl-NR$_{23}$—C(O)—, phenyl-NR$_{23}$—S(O)$_2$—, phenyl-S(O)—, phenyl-S(O)$_2$—, phenyl-CO$_2$—, phenyl-S(O)—O—, phenyl-SO$_3$—, phenyl-NR$_{23}$—, and phenyl-CH=CH—; or $R_{17}$ and $R_{18}$ together, $R_{19}$ and $R_{20}$ together $R_{17}$ and $R_{18}$ together and $R_{19}$ and $R_{20}$ together, or $R_{18}$ and $R_{19}$ together are selected from the groups —CH=CR$_{24}$—CR$_{25}$=CH—N=CR$_{24}$—CR$_{25}$=CH—, —CH=CR$_{24}$—CR$_{25}$=N—, —CH=N—CR$_{25}$=CH—, —CH=CR$_{24}$—N=CH—, —N=CR$_{24}$—N—, —N=CR$_{24}$—N=CH—, —CH=CH—O—, —CH=CH—S—, and —CH=CH—NR$_{23}$—;

$R_{21}$ and $R_{22}$ independently from one another are $C_1$ to $C_{20}$alkyl, phenyl, $C_1$ to $C_{12}$alkylphenyl, benzyl or $C_1$ to $C_{12}$alkylbenzyl, or $R_{21}$ and $R_{22}$ together mean tetramethylene, pentamethylene or —CH$_2$CH$_2$—O—CH$_2$CH$_2$—;

$R_{23}$ is H, $C_1$ to $C_4$alkyl or benzyl; and $R_{24}$ and $R_{25}$ are independently from one another H, $C_1$ to $C_6$alkyl, $C_1$ to $C_6$alkoxy, $C_1$ to $C_6$alkylthio, or F, Cl or Br.

2. A compound according to claim 1, characterized in that it corresponds to formula VI,

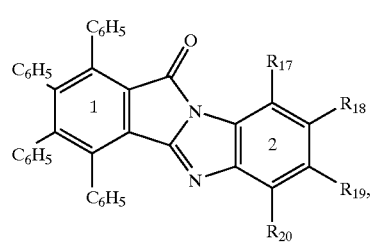

(VI)

wherein $R_{17}$ and $R_{20}$ are H, and $R_{18}$ and $R_{19}$ or both are $C_1$ to $C_{18}$alkyl or $C_1$ to $C_{18}$ alkoxy, or $R_{18}$ and $R_{19}$ together mean —CH=CR$_{24}$—CR$_{25}$=CH—; or $R_{17}$ and $R_{18}$ together or $R_{19}$ and $R_{20}$ together $R_{17}$ and $R_{18}$ together and $R_{19}$ and $R_{20}$ together mean —CH=CR$_{24}$—CR$_{25}$=CH—, wherein $R_{24}$ and $R_{25}$ are independently from one another H, F, Cl, $C_1$ to $C_8$alkyl or $C_1$ to $C_8$alkoxy.

* * * * *